(12) United States Patent
Min et al.

(10) Patent No.: US 8,090,443 B2
(45) Date of Patent: Jan. 3, 2012

(54) MONITORING HF EXACERBATION AND CARDIAC RESYNCHRONIZATION THERAPY PERFORMANCE

(76) Inventors: Xiaoyi Min, Thousand Oaks, CA (US); Zaffer Syed, Valencia, CA (US)

( * ) Notice: Subject to any disclaimer, the term of this patent is extended or adjusted under 35 U.S.C. 154(b) by 537 days.

(21) Appl. No.: 12/210,880

(22) Filed: Sep. 15, 2008

(65) Prior Publication Data
US 2010/0069987 A1    Mar. 18, 2010

(51) Int. Cl.
*A61N 1/365* (2006.01)

(52) U.S. Cl. ............................................. 607/17; 607/9

(58) Field of Classification Search ........................ None
See application file for complete search history.

(56) References Cited

U.S. PATENT DOCUMENTS

| 6,438,408 | B1 | 8/2002 | Mulligan et al. |
| 6,748,261 | B1 | 6/2004 | Kroll et al. |
| 7,702,390 | B1 * | 4/2010 | Min .................................. 607/9 |
| 7,778,706 | B1 * | 8/2010 | Min .................................. 607/9 |
| 2004/0122484 | A1 | 6/2004 | Hatlestad et al. |
| 2004/0122485 | A1 | 6/2004 | Stahmann et al. |
| 2004/0122486 | A1 | 6/2004 | Stahmann et al. |
| 2004/0122487 | A1 | 6/2004 | Hatlestad et al. |

FOREIGN PATENT DOCUMENTS

| EP | 1345651 B1 | 3/2006 |
| WO | 02053228 A1 | 7/2002 |

* cited by examiner

*Primary Examiner* — Kennedy Schaetzle

(57) ABSTRACT

An exemplary method includes delivering a cardiac resynchronization therapy using an atrio-ventricular delay parameter and an interventricular delay parameter, measuring an atrio-ventricular conduction delay, measuring an interventricular conduction delay, assessing heart failure and/or cardiac resynchronization therapy performance based at least in part on the measured atrio-ventricular conduction delay and the measured interventricular conduction delay and determining at least one of an atrio-ventricular delay parameter value and an interventricular delay parameter value based at least in part on the measured atrio-ventricular conduction delay and the measured interventricular conduction delay. Other exemplary technologies are also disclosed.

20 Claims, 14 Drawing Sheets

MONITORING HF EXACERBATION AND CARDIAC RESYNCHRONIZATION THERAPY PERFORMANCE

TECHNICAL FIELD

Exemplary technologies presented herein generally relate to cardiac pacing and/or stimulation therapy. Various techniques provide for monitoring cardiac condition and therapy performance.

BACKGROUND

Heart Failure (HF) is a chronic condition that affects over 5 million Americans and, according to the American Heart Association, HF accounts for more hospitalization among elderly people than any other condition. HF is not a condition in which the heart abruptly stops beating. Instead, HF refers to a dysfunction in the pumping action of the heart due to the heart's inability to contract or relax properly. It is generally experienced by patients who have suffered a heart attack or whose hearts have been damaged by other conditions which have disrupted the heart's natural electrical conduction system.

Patients with heart failure generally experience breathlessness, fatigue and fluid build-up in the arms and legs. This is caused by the heart's inability to pump enough blood to meet the body's demands. The heart can become enlarged as it attempts to compensate for the lack of pumping ability, which only worsens the condition. Typically, it is the lower chambers of the heart (ventricles) that do not beat efficiently (e.g., ventricular dyssynchrony) resulting in an increasingly ineffective heart. However, with HF, the upper chambers (atria) can also become enlarged or experience disruption in electrical conduction (e.g., atrial dyssynchrony).

The right ventricle is responsible for pumping blood to the lungs while the left ventricle is responsible for pumping blood to the rest of the body. The right atrium fills the right ventricle with deoxygenated blood while the left atrium fills the left ventricle with oxygenated blood. In a normal heart, the atria contract to fill the ventricles and then the ventricles contract in a synchronous manner to pump blood through the lungs or the body. Abnormal activation of any of the heart's four chambers reduces pumping efficiency. For example, abnormal ventricular activation can decrease ventricular filling, cause abnormal ventricular wall motion and cause mitral valve regurgitation (MR). Standard pharmacologic therapy cannot adequately resolve conduction and activation abnormalities such as left bundle branch block (LBBB) or a lengthy interventricular conduction delay (IVCD) that contribute to ventricular dyssynchrony.

Cardiac Resynchronization Therapy (CRT) provides an electrical solution to the symptoms and other difficulties brought on by HF. In many CRT systems, electrical impulses can be delivered to the tissue in the heart's two lower chambers (and typically one upper chamber). This is called biventricular pacing, and it causes the ventricles to beat in a more synchronized manner. Biventricular pacing improves the efficiency of each contraction of the heart and the amount of blood pumped to the body. This helps to lessen the symptoms of heart failure and, in many cases, helps to stop the progression of the disease. For patients fitted with CRT systems, clinical studies show improved quality of life (QOL), NYHA functional class, exercised tolerance, left ventricular reverse remodeling, morbidity and mortality.

For proper operation, values for a handful of CRT system parameters must be determined. In general, a clinician determines such values using information acquired from an echocardiography examination of a patient. Once the parameter values have been determined, the clinician can then program the patient's implantable CRT device. Some newer CRT systems include algorithms that can determine CRT parameter values based on cardiac electrograms measured by a patient's implantable CRT device. For example, the QUICKOPT™ algorithm (St. Jude Medical Corporation, Sylmar, Calif.) can determine AV, PV, and VV intervals in about a minute using intracardiac electrogram (IEGM) information. Noting that clinical evidence demonstrates that timing cycle optimization improves outcomes to CRT therapy and that optimal delays change over time, the QUICKOPT™ algorithm allows for efficient, frequent optimization. Further, QUICKOPT™ optimization is clinically proven to correlate with echo based techniques.

As described herein, various exemplary techniques acquire information (e.g., measurements and/or parameter values) and analyze such information to monitor cardiac condition and/or CRT performance. In turn, knowledge of cardiac condition and/or CRT performance can be used to optimize patient therapy.

SUMMARY

An exemplary method includes delivering a cardiac resynchronization therapy using an atrio-ventricular delay parameter and an interventricular delay parameter, measuring an atrio-ventricular conduction delay, measuring an interventricular conduction delay, assessing heart failure and/or cardiac resynchronization therapy performance based at least in part on the measured atrio-ventricular conduction delay and the measured interventricular conduction delay and determining at least one of an atrio-ventricular delay parameter value and an interventricular delay parameter value based at least in part on the measured atrio-ventricular conduction delay and the measured interventricular conduction delay. Other exemplary technologies are also disclosed.

In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Exemplary techniques pertain generally to monitoring cardiac condition and cardiac resynchronization therapy (CRT) performance. In particular, such techniques may be implemented in a post-operative phase to improve outcomes for patients undergoing CRT. For example, an implantable CRT device can acquire information that can be used to assess cardiac condition, to assess CRT performance, to optimize CRT or other patient therapies, and/or to issue medical alerts.

Exemplary Stimulation Device

The techniques described below are intended to be implemented in connection with any stimulation device that is configured or configurable to stimulate nerves and/or stimulate and/or shock a patient's heart.

Figure 1:
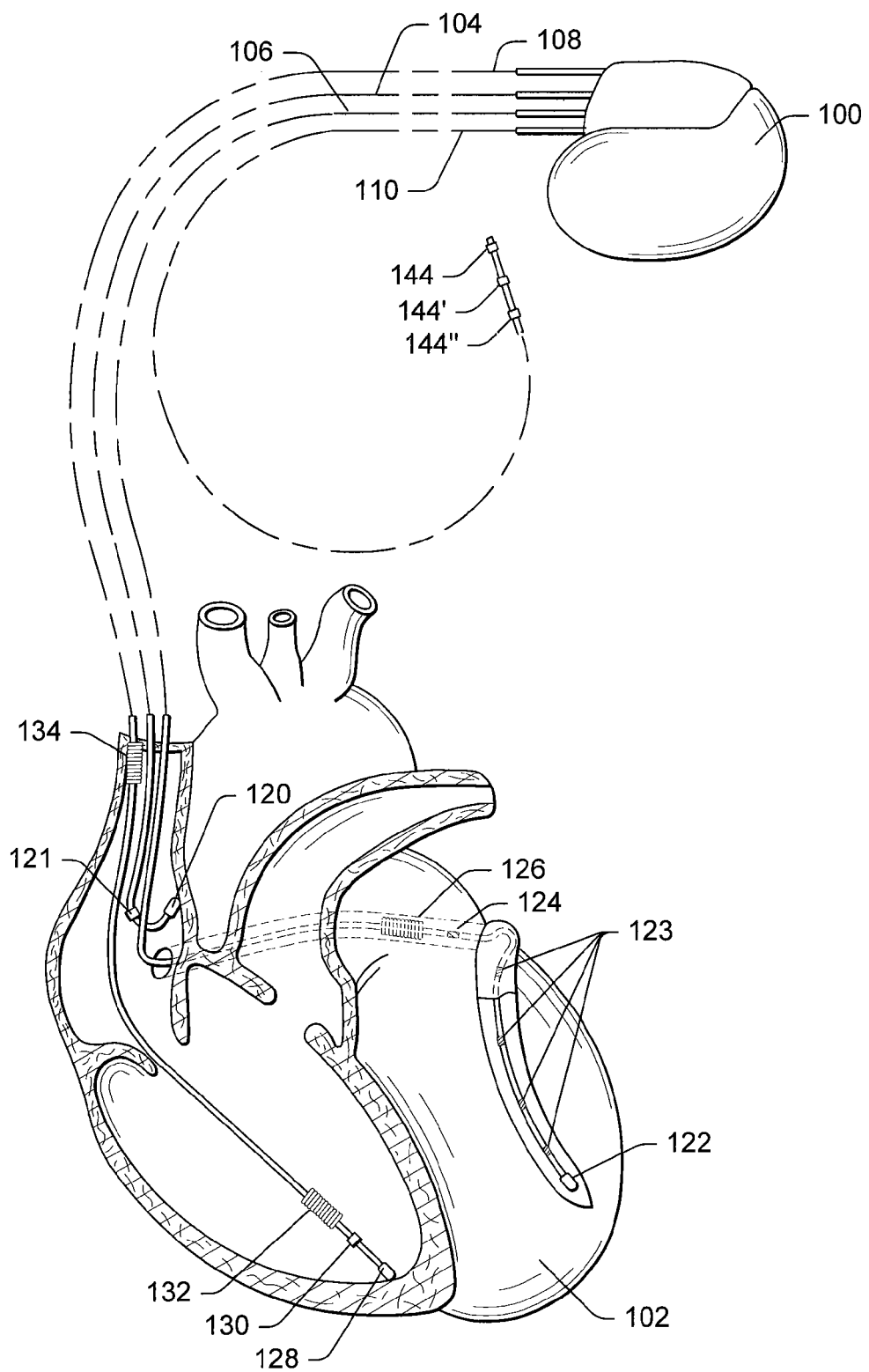
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation therapy and optionally shock therapy. In the example of FIG. 1, the device 100 includes a fourth lead 110 having, in this implementation, three electrodes 144, 144', 144" suitable for stimulation of tissue (e.g., myocardial tissue, muscle tissue, autonomic nerves, etc.) and/or sensing information. Lead number, lead type, electrode number, etc., can vary depending on the particular therapy or therapies to be delivered to a patient.

The right atrial lead 104 is configured to be positioned in a patient's right atrium. The implantable device 100 can use the right atrial lead 104 for delivering stimulation therapy to the right atrium. The right atrial lead 104 may also be configured to allow the device 100 to sense cardiac signals (e.g., near field atrial signals and/or far field ventricular signals). As shown in FIG. 1, the right atrial lead 104 includes an atrial tip electrode 120 (typically implanted in the patient's right atrial appendage) and an atrial ring electrode 121. The right atrial lead 104 may include one or more additional electrodes.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or a tributary vein of the coronary sinus. As shown in FIG. 1, the coronary sinus lead 106 is positioned in the coronary sinus and a tributary to the coronary sinus where at least one electrode is adjacent to the left ventricle and at least one additional electrode is adjacent to the left atrium.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

An exemplary coronary sinus lead 106 can be designed to receive ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the superior vena cava (SVC) coil electrode 134 will be positioned in the SVC. Accordingly, the right ventricular lead 108 is capable of sensing or receiving cardiac signals and delivering stimulation in the form of pacing and shock therapy to the right ventricle. An exemplary right ventricular lead may also include at least one electrode capable of stimulating an autonomic nerve, non-myocardial tissue, other nerves, etc., where such an electrode may be positioned on the lead or a bifurcation or leg of the lead. A right ventricular lead may include a series of electrodes, such as the series 123 of the left ventricular lead 106.

Figure 2:
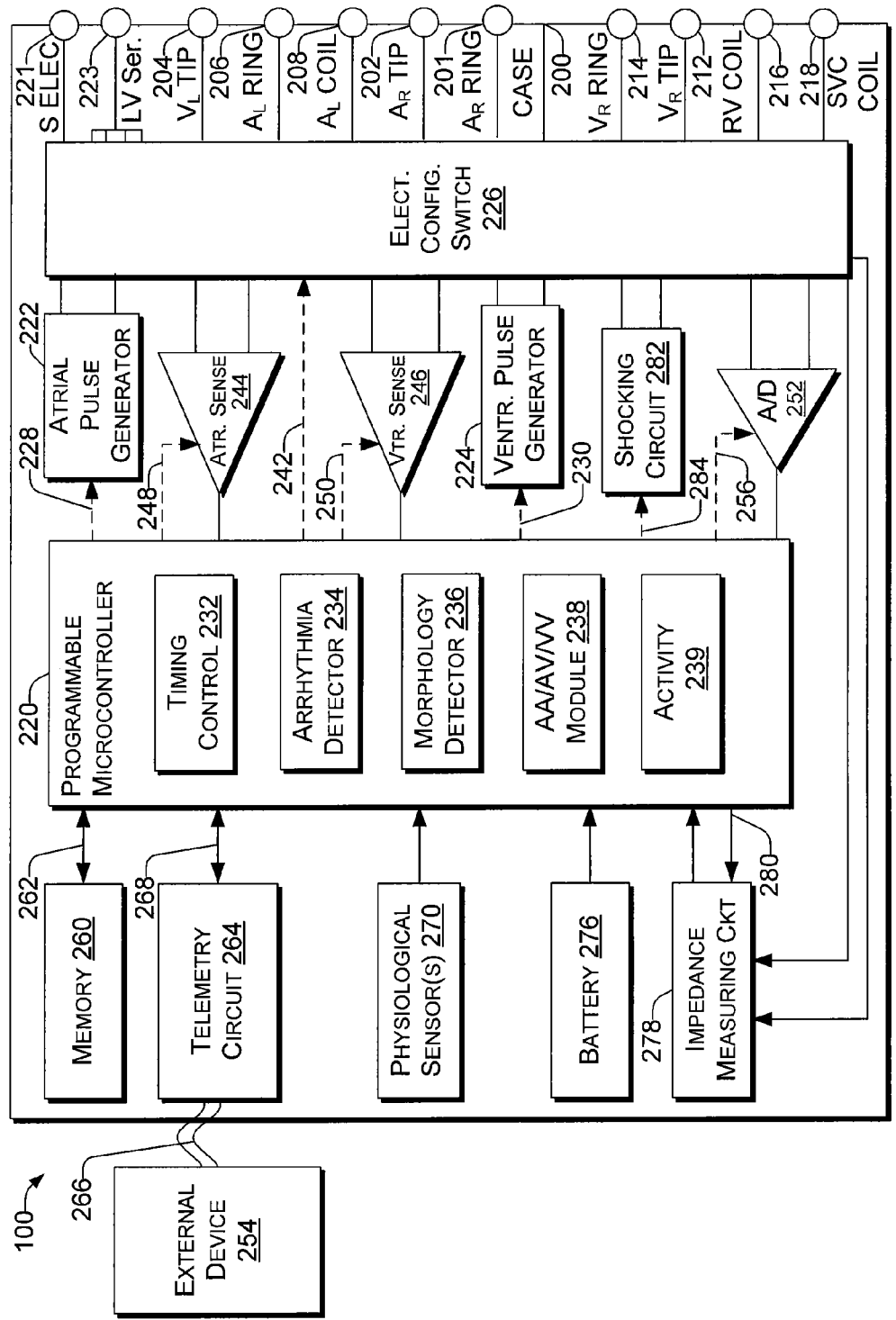
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy (e.g., cardioversion, defibrillation, and/or pacing stimulation). While a particular multi-chamber device is shown, it is to be appreciated and understood that this is done for illustration purposes only. Techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation and/or pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. In general, housing 200 may be used as an electrode in any of a variety of electrode configurations. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121.

To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

Connection to suitable autonomic nerve stimulation electrodes is also possible via aforementioned terminals and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, bi-ventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. Such a module may help make determinations as to fusion.

The microcontroller 220 of FIG. 2 also includes an activity module 239. This module may include control logic for one or more activity related features. For example, the module 239 may include an algorithm for determining patient activity level, calling for an activity test, calling for a change in one or more pacing parameters, etc. These algorithms are described in more detail with respect to the figures. The module 239 may be implemented in hardware as part of the microcontroller 220, or as software/firmware instructions programmed into the device and executed on the microcontroller 220 during certain modes of operation. The module 239 may act cooperatively with the AA/AV/VV module 238.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram (IEGM) signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the optional lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. The device 100 typically includes the ability to sense and store a relatively large amount of data (e.g., from the data acquisition system 252), which data may then be used for subsequent analysis, for example, to guide the programming of the device.

Various types of information (e.g., parameter values, modes, etc.) for the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 allows intracardiac electrograms (IEGMs) and status information relating to the operation of the device 100 (as contained in the microcontroller 220 or memory 260) to be sent to the external device 254 through an established communication link 266.

The stimulation device 100 can include one or more physiological sensors 270. For example, the device 100 may include a "rate-responsive" to adjust pacing stimulation rate according to the exercise state of the patient. The device 100 may include a physiological sensor 270 to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). The microcontroller 220 may be programmed to respond to sensed information by adjusting one or more therapy parameters (such as rate, AA delay, AV delay, VV delay, etc.).

While the block 270 is shown as being included within the stimulation device 100, it is to be understood that a physiologic sensor may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance. For example, an activity sensor may be monitored diurnally to detect the low variance in a measurement as corresponding to a patient's sleep state. For a complete description of an activity variance sensor, the reader is directed to U.S. Pat. No. 5,476,483 (Bornzin et al.), issued Dec. 19, 1995, which patent is hereby incorporated by reference.

The one or more physiological sensors 270 optionally include sensors for detecting minute ventilation and/or sensors for detecting movement and/or position. A minute ventilation (MV) sensor senses minute ventilation, which is defined as the total volume of air that moves in and out of a patient's lungs in a minute. A movement and/or position sensor may rely on spring loaded moving mass(es) that responds to movement (e.g., acceleration) and/or patient position (e.g., angle with respect to acceleration of gravity). Signals generated by a sensor can be passed to the microcontroller 220 for analysis in determining whether to adjust one or more settings (e.g., AV delay, VV delay, pacing rate, etc.). For example, the microcontroller 220 may monitor a sensor's signal for indications of a patient's position and/or activity status, such as whether the patient is climbing upstairs or descending downstairs or whether the patient is sitting up after lying down, and adjust one or more settings to accommodate the patient's activity.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring edema; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Exemplary Method

Figure 3:
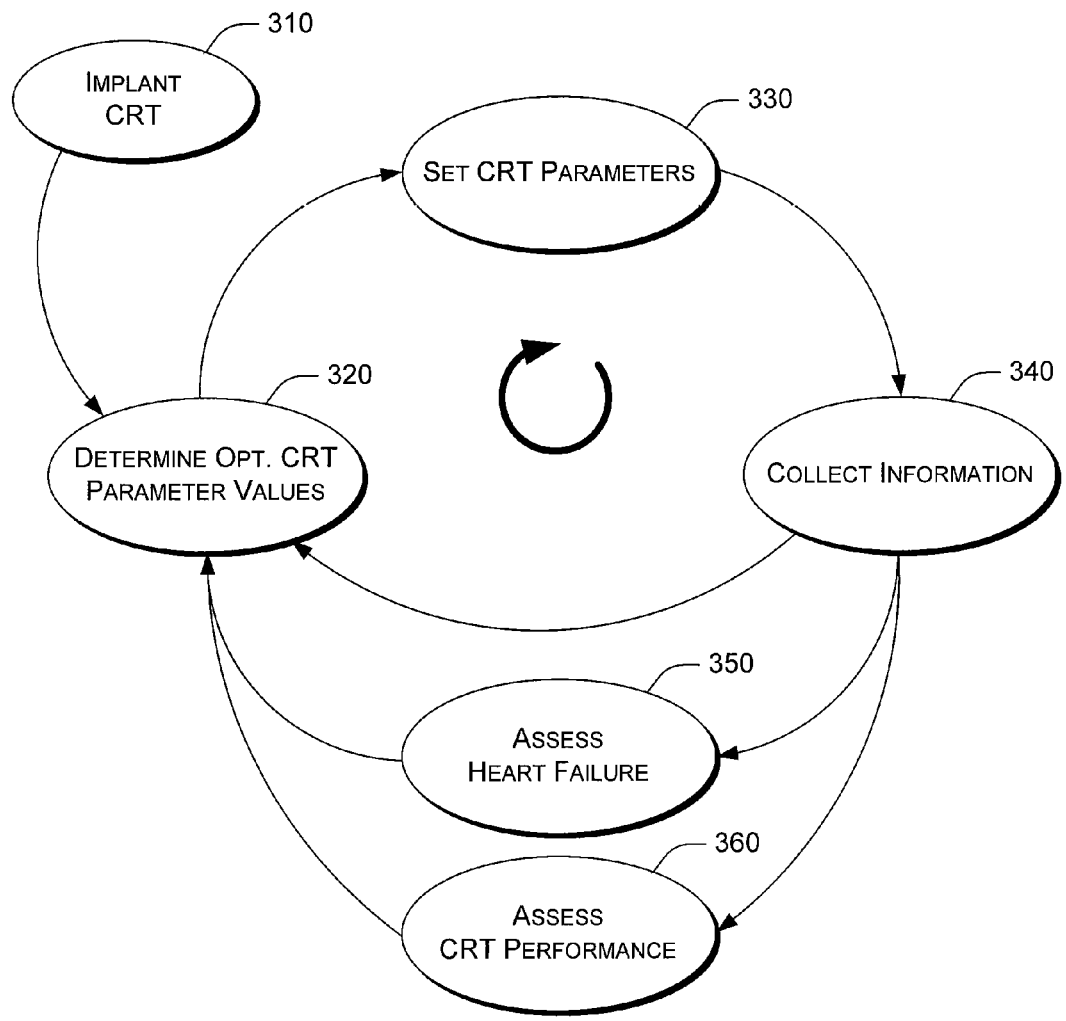
FIG. 3 is a diagram of an exemplary method for monitoring heart failure and/or CRT performance.

FIG. 3 shows an exemplary method 300 for assessing HF and CRT performance. The method 300 includes an implantation step 310 for implanting a CRT device in a patient. Patients undergoing implantation of a CRT device require comprehensive, preoperative evaluations to reduce patient risk and increase implant success. A thorough evaluation of cardiac performance (e.g., echocardiogram, cardiac catheterization) normally occurs prior to implantation to quantify atrial and ventricular chamber sizes, valve function, and left ventricular ejection fraction. A surface electrode electrocardiogram can identify abnormal AV conduction, widened QRS complexes and other cardiac conditions. Such tests are particularly important for patients with advanced HF, which are generally at a higher risk for adverse events during and after the device implant.

After implantation, a determination step 320 determines optimum parameter values for operation of the CRT device. A parameter or a setting may refer to a function parameter such as an on/off parameter or to a timing parameter such as an AV delay. For a function parameter, the value may be a "0" to indicate "off" or a "1" to indicate "on" whereas for a timing parameter, the value will usually be, or correspond to, a time or a time interval. Thus, the determination step 320 may determine what CRT device capabilities to use for a particular patient and physical values such as timings, amplitudes, etc., for delivery of CRT. The determination step 320 may rely on one or more computing devices, as explained with respect to FIGS. 4 and 5.

In the method 300, a set step 330 sets CRT parameters according to the values provided by the determination step 320. The implanted CRT device then delivers CRT using the set parameters. An information collection step 340 collects information, which may include CRT parameter information, information measured by the implanted CRT device (e.g., IEGMs) and/or other information such as information measured by one or more other devices (e.g., implanted or external).

The method 300 includes a HF assessment step 350 and a CRT performance assessment step 360. While these two steps are shown separately, as explained, for example, in FIG. 13, such assessments may occur in a coordinated manner. More specifically, an HF assessment may depend on a CRT performance assessment and vice versa. As indicated in FIG. 3, the determination step 320 may rely on the assessment steps 350, 360 and/or the information collection step 340.

The method 300 includes one or more loops that can occur periodically, according to a schedule, in response to an event, etc. For example, a loop that includes steps 320, 330 and 340 may occur periodically while a loop that includes the step 350 and/or the step 360 may occur in response to an event (e.g., an alert, a command issued by a clinician, etc.). The method 300 may be performed in a patient environment and/or in a clinician environment as explained with respect to FIGS. 4 and 5.

Figure 4:
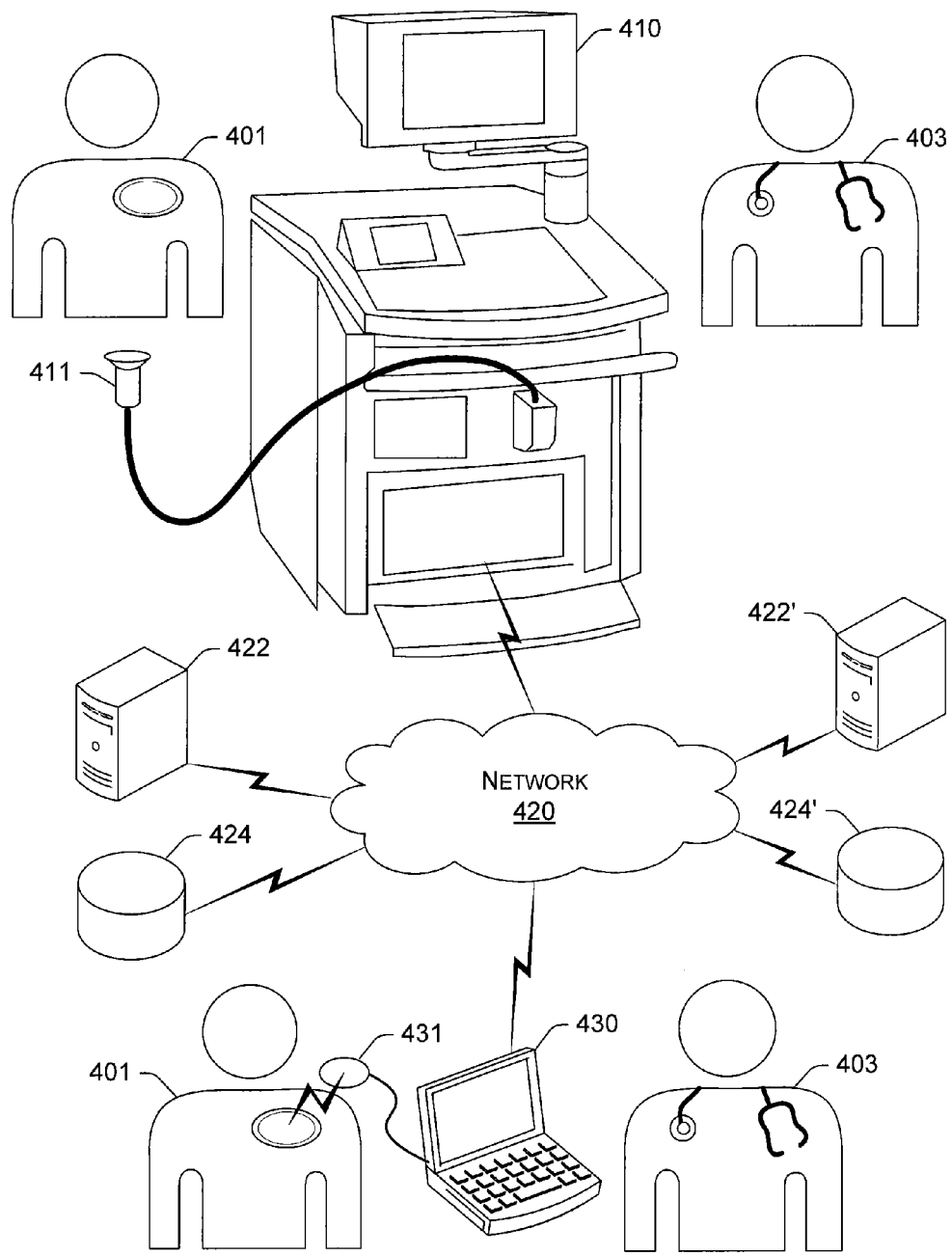
FIG. 4 is a diagram of an exemplary system for determining one or more CRT settings that includes echocardiography equipment and a computing device in a clinician environment.

FIG. 4 shows an exemplary system 400 for performing various steps of the method 300. The system 400 includes diagnostic equipment 410 and a device programmer 430 that reside in a clinician environment. In this example, a clinician 403 can acquire echocardiograms for a patient 401 using the diagnostic equipment 410. An echocardiogram relies on ultrasound measurements to provide insight as to characteristics of the heart, including performance. For example, an echocardiogram can indicate size of the chambers of the heart, including the dimension or volume of a chamber and wall thickness. In patients with long standing hypertension or high blood pressure, a echocardiogram can help determine "stiffness" of chamber walls. For HF patients, where LV pump function is reduced, the LV and the RV tend to dilate or enlarge; an echocardiogram can measure the severity of this enlargement. A series of echocardiograms (e.g., performed on an annual basis) can be used to gauge the heart's response to a particular therapy.

With respect to pumping function of the heart, an echocardiogram can be used to determine ejection fraction (EF). A normal EF is typically around 55 to 65% while values below 45% usually represent some decrease in the pumping strength of the heart. EF values below 30 to 35% indicate a significant decrease in pumping strength.

An echocardiogram is usually performed in a clinic or a hospital, i.e., a clinician environment. In most instances, an electrocardiogram (ECG) is acquired along with an echocardiogram to help identify timing of various cardiac events (filling and emptying of chambers). The clinician 403 preps the patient 401 by positing appropriate ECG electrodes and by applying a gel to the patient's chest, which helps the transducer 411 transmit and receive ultrasound. During an examination, the clinician 403 may ask the patient 401 to move form back to side or to another position. Instructions may also be given to the patient 401 for controlling breath (e.g., to breathe slowly or to hold her breath), for example, to increase echo data quality. Throughout the examination, the clinician 403 can view echo-based images on a monitor. The clinician 403 may record the echo data locally and/or remotely for later review. The entire examination process, which requires a skilled clinician, typically takes about 30 minutes to an hour, not including patient transit and wait time (e.g., driving to the clinic, waiting in a lobby, etc.).

With respect to the method 300, information acquired from an echocardiograpy examination may be used in the determination step 320 for determining optimal CRT parameters prior to or after implant. If such an examination occurs after implant (e.g., in a post-operative phase), the examination may be part of the information collection step 340. The information collection step 340 may proceed to the determination step 320, the HF assessment step 350 and/or the CRT performance assessment step 360.

In the example of FIG. 4, information acquired from an echocardiograph examination can be used to program a patient's CRT device. As shown, the system 400 includes a network 420 that can be used to transmit echocardiography information to one or more computing devices 422, 422' or data storage devices 424, 424'. The network 420 may be an intranet for a clinic, a hospital, etc., or may be a broader network that includes the Internet. Communication of information may occur via physical connections or wireless connections.

The system 400 includes a device programmer 430 that can establish a communication link with the network 420. The clinician 403 can acquire echocardiography information and/or other information via the network 420 to aid in programming the implanted CRT device of the patient 401. For example, the device programmer 430 may pull patient data from a data storage device 424 controlled via a network server 422. Such data may include information from prior echocardiography examinations. The device programmer 430 may also acquire information from the patient's implanted CRT device using a wand or paddle 431 that includes appropriate communication circuitry.

The patient 401 may be in an acute post-operative phase where an echocardiogram is acquired before discharge from the hospital or the patient 401 may be in a chronic post-operative phase where an echocardiogram is acquired during a follow-up visit to a clinic. In either instance, the clinician 403 may use the device programmer 430 and the echocardiography information to adjust PV/AV and VV parameters, for example, to reduce mitral regurgitation, maximize left ventricular diastolic filling, etc.

Referring again to the method 300 of FIG. 3, the device programmer 430 will normally perform the steps 320, 330 and 340 and optionally the steps 350 and 360. However, an exemplary CRT device such as the device 100 of FIGS. 1 and 2, may be configured to receive echocardiography information and to perform steps 320 and 330 based on such information. An exemplary CRT device may also be configured to perform the assessment steps 350 and 360 based on received echocardiography information. Again, where echocardiography information is required, the patient 401 must normally visit a clinic or hospital.

Figure 5:
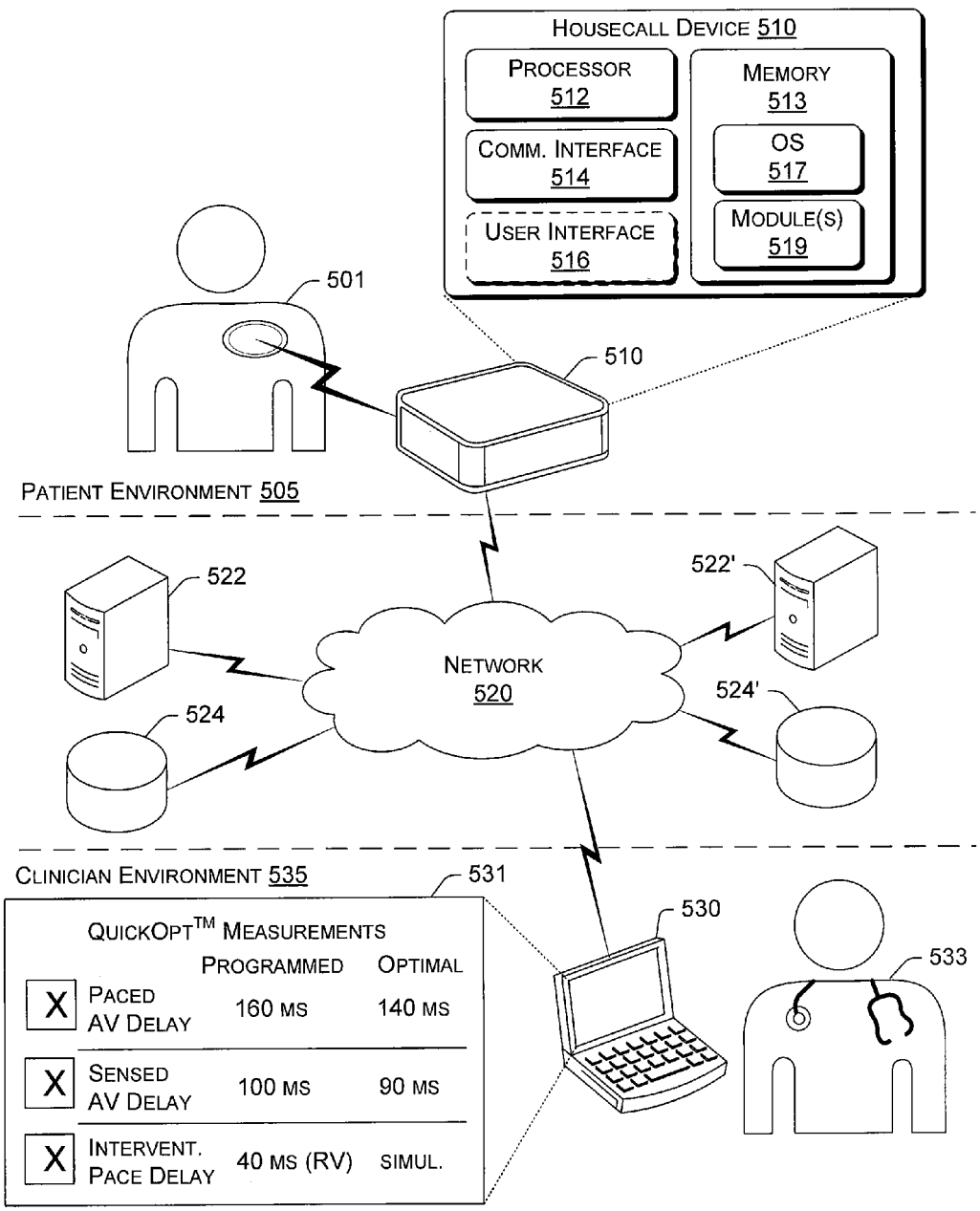
FIG. 5 is a diagram of an exemplary system for determining one or more CRT settings that includes a house call device in a patient environment and a computing device in a clinician environment.

FIG. 5 shows an exemplary system 500, which differs from the system 400. In particular, for the system 500, a patient 501 resides in a patient environment 505 while a clinician 533 resides in a clinician environment 535. Thus, according to the system 500, the patient 501 does not need to visit a clinic or a hospital. Further, the system 500 can operate without a need for echocardiography examinations. More specifically, the system 500 can optimize CRT parameter values without echocardiography information. Thus, the patient 501 can simply stay at home (i.e., in the patient environment 505) and have CRT parameter values set to optimal values according to need and/or a schedule. Further, the clinician 533 may perform tasks related to the patient's treatment without having to coordinate patient-clinician schedules. Accordingly, the system 500 can greatly reduce patient and clinician burdens and allow for more frequent optimization of CRT, monitoring, assessment, etc.

The system 500 includes a housecall device 510 in the patient environment 505. The housecall device 510 includes a processor 512, a communication interface 514 and memory 513 and optionally a user interface 516. The memory 513 stores an operating system 517 and one or more other instruction modules 519. The operating system 517 allows the processor 512 to operate according to instructions provided by an instruction module 519. In general, an instruction module 519 includes software instructions that allow the device 510 to communicate via the communication interface 514 and to optionally display or receive information via the optional user interface 516. The communication interface 514 provides for communication with an implantable CRT device and for communication with a network 520, which may occur via wire/cable and/or wirelessly. The instruction module 519 may include interrogator instructions for interrogating the patient's implantable CRT device and processing instructions to perform one or more of the steps of the method 300 of FIG. 3.

With respect to device configurations, the housecall device 510 may be a unit with or without a visual display panel. The device 510 may be battery powered, powered by house current, powered by a fuel cell, powered by a vehicle's power supply, solar powered, etc. The housecall device 510 may include a wand with communication circuitry. In such instances, the patient 501 or a caretaker may position the wand for communication with the patient's implantable CRT device. The housecall device 510 may include circuitry for detecting range or proximity of the patient's implantable CRT device. For example, if positioned at bedside, the housecall device 510 may communicate with the patient's CRT device while the patient is in bed. In this example, communication may occur on a nightly basis.

The system 500 includes a network 520 that allows for communication between the housecall device 510 in the patient environment 505 and a computing device 530 in the clinician environment 535. The network 520 may link to one or more additional computing devices 522, 522' and/or data storage devices 524, 524'.

The computing device 530 may be configured to perform one or more steps of the method 300. As shown, the computing device 530 is configured to display a graphical user interface (GUI) 531 to assist in optimizing the patient's CRT. The GUI 531 may be part of a Web browser interface for the computing device 530 where one or more CRT-related algorithms execute on another computing device. In the example of FIG. 5, the GUI 531 displays a variety of parameters and parameter values, including programmed and optimal paced AV delay, programmed and optimal sensed AV delay and programmed and optimal interventricular pace delay. Parameter values for CRT may be determined by one or more of the following: (i) the patient's CRT device, (ii) the housecall device 510, (iii) the computing device 530 and (iv) computing devices linked to the network 520. Regardless of the location or locations at which parameter values are determined, the computing device 530 allows the clinician 533 to intervene in the patient's therapy.

With respect to the assessment steps 350 and 360 of FIG. 3, the system 500 may perform these steps using one or more of the computing devices 510, 522, 522', 530. The patient's CRT device may include instructions for performing the HF assessment step 350 and/or the CRT performance assessment step 360.

Figure 6:
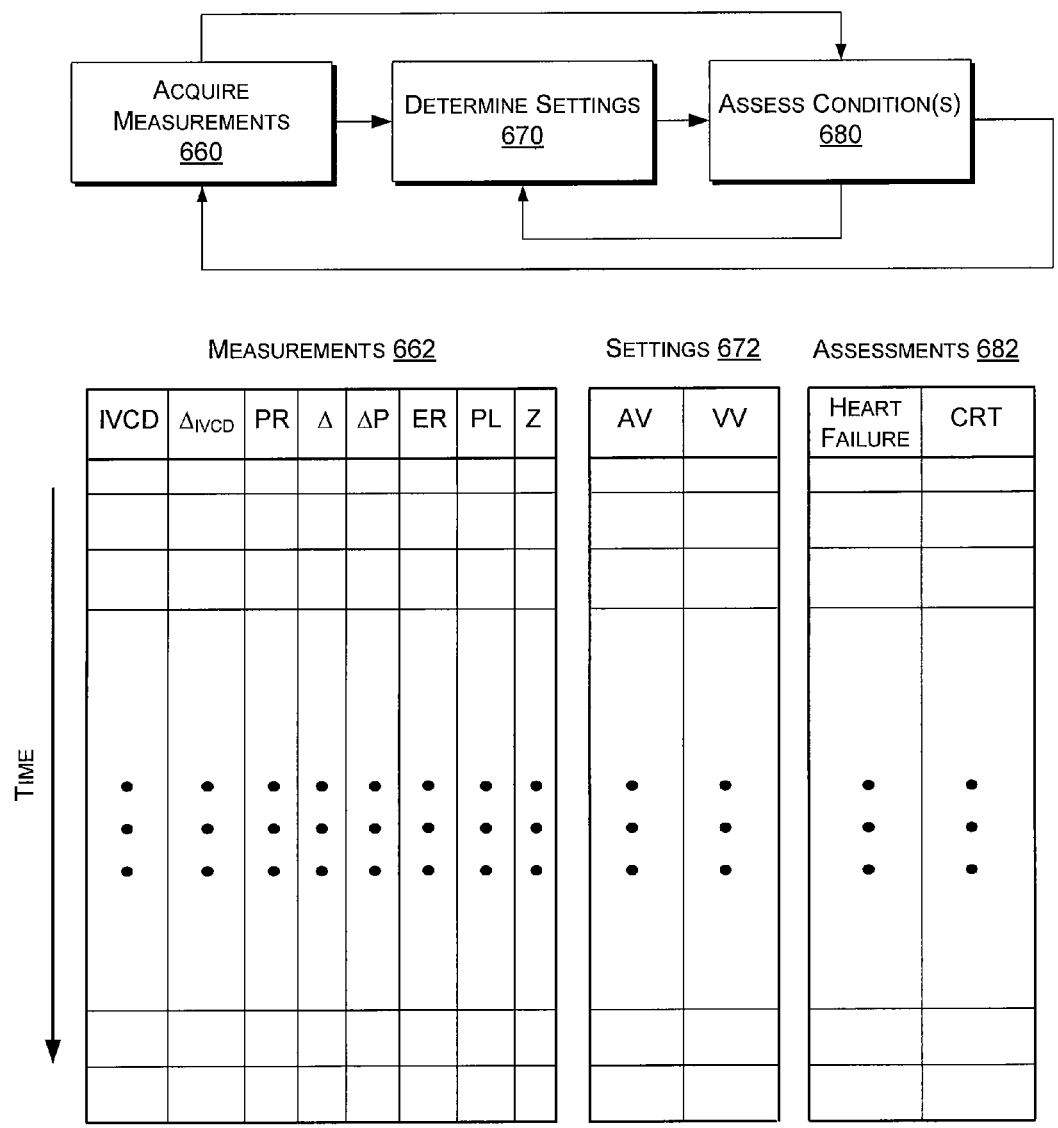
FIG. 6 is a block diagram of an exemplary method and associated types of information.

FIG. 6 shows an exemplary method 600 and various associated measurement parameters 662, setting parameters 672 and assessment parameters 682. The method 600 may be implemented by the system 400 or the system 500. According to the method 600, an acquisition block 660 acquires measurements, a determination block 670 determines CRT settings and an assessment block 680 assesses HF and/or CRT performance.

With respect to acquisition of measurements, these may correspond to one or more of the measurement parameters 662. In particular, the measurements may include interventricular conduction delay (IVCD), the difference between left to right and right to left interventricular conduction delay ($\Delta_{IVCD}$), PR/AR interval, $\Delta$ (e.g., $PR_{LV}-PR_{RV}$), one or more evoked response characteristics (ER), pacing latency (PL) and/or impedance (Z). Each of these measurements includes information as to condition of the heart. For example, scar tissue associated with ischemia or infarct can alter conduction. Thus, if scar tissue arising along an interventricular conduction path, then IVCD will change. With respect to evoked response, an increase in conduction heterogeneity can cause evoked response amplitude to diminish and evoked response duration to increase. With respect to pacing latency, if conduction near a pacing electrode decreases, then the pacing latency may increase. With respect to impedance, damage to myocardial tissue can affect impedance measured between electrodes separated by the myocardial tissue. Impedance measurements across the lung tissue or other tissues may be indicative of pulmonary or other conditions that affect HF and/or CRT performance. While various examples are given for deteriorating conditions, such measurements may also provide evidence as to improvements in HF and/or CRT performance.

Figure 7:
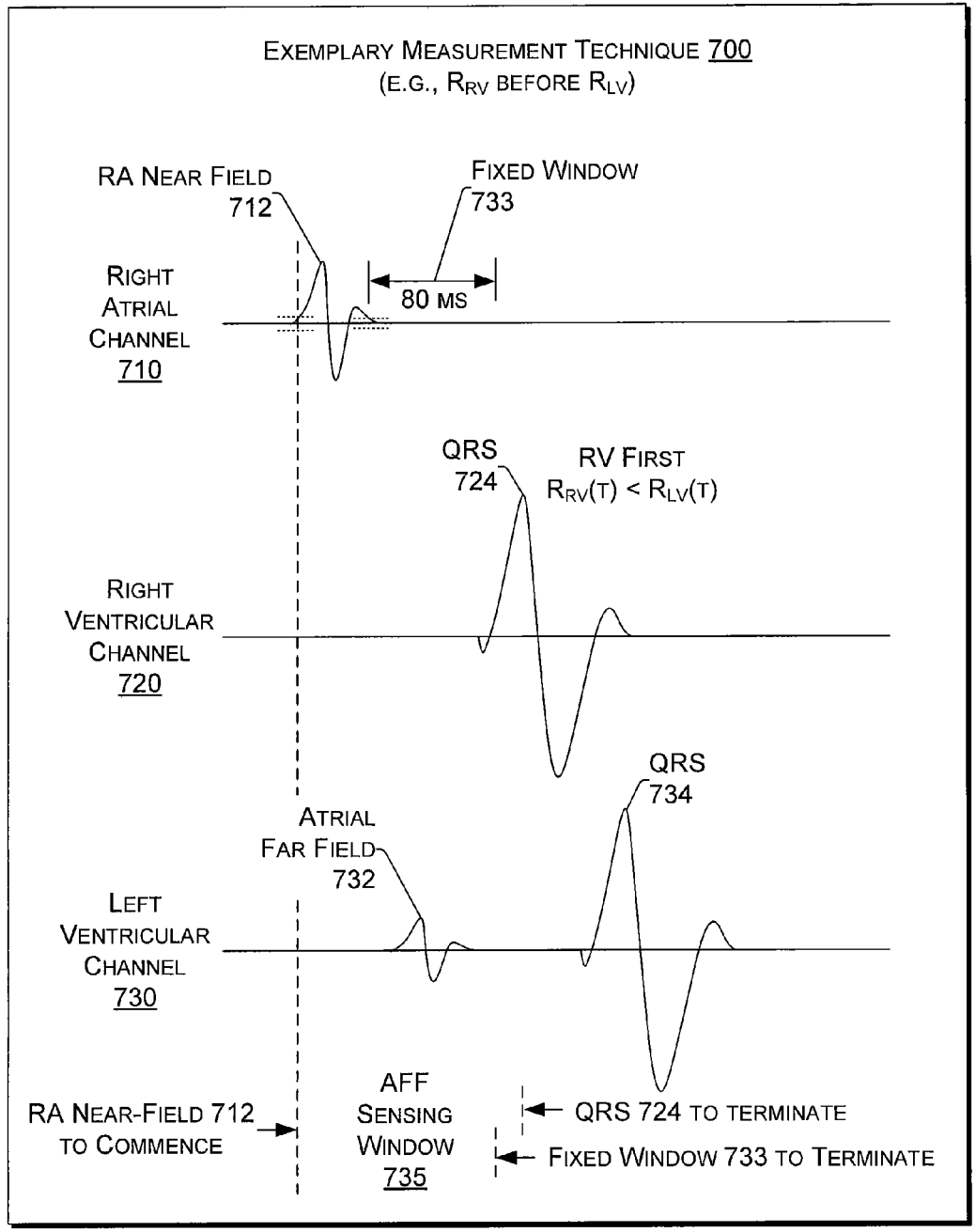
FIG. 7 is a diagram of various sensing channels to illustrate a technique for acquiring far-field atrial information.

FIG. 7 shows an exemplary technique 700 for measuring atrial information, especially atrial information that reflects left atrial activity as well as right atrial activity. The technique 700 is illustrated using information acquired via a right atrial sensing channel 710, a right ventricular sensing channel 720 and a left ventricular sensing channel 730. The technique 700 can be implemented using various mechanisms to initiate and to terminate an atrial far-field sensing window 735. As shown in FIG. 1, the right atrial lead 104 allows for positioning of electrodes in the right atrium and near-field sensing of atrial activity. As indicated on the right atrial channel 710, a near-field signal 712 acquired using electrodes positioned in the right atrium (e.g., electrodes 120 and 121) reflects primarily right atrial activity. Hence, the near-field signal 712 provides information germane to right atrial function. While knowledge of right atrial function can help in setting parameter values, many cardiac conditions are more intimately associated with left atrial function.

According to the technique 700, an atrial far-field (AFF) sensing window 735 allows for acquisition of information germane, at least in part, to left atrial function. The AFF sensing window 735 can be established based on information acquired using a right atrial channel signal 712 and a predetermined interval (e.g., fixed window 733) or information acquired using a ventricular channel signal (e.g., QRS 724).

For example, information in the right atrial channel signal 712 can be used to initiate the AFF sensing window 735 and a fixed window 733 or information in a ventricular signal (e.g., in QRS 724) can be used to terminate the AFF sensing window 735.

The fixed window 733 may be in a range from about 60 ms to about 120 ms or more particularly about 80 ms to about 100 ms when commencing from the end of the near-field right atrial signal; noting that the AFF sensing window 735 is initiated earlier. A fixed window may be longer where it commences earlier (e.g., from beginning or peak of a right atrial signal). Further, a fixed window may set the entire AFF sensing window, for example, where the fixed window (and the AFF sensing window) commences near the beginning of the near-field right atrial signal.

An exemplary technique may compare the QRS time to the fixed window time and choose the earlier of the two to terminate the AFF sensing window 735. An exemplary technique may determine whether the right ventricle or left ventricle contracts first (e.g., using a distal LV lead electrode) to decide whether a right ventricular channel signal or a left ventricular channel signal should be used to terminate the AFF sensing window 735.

As CHF patients suffer more commonly from LBBB as opposed to RBBB, the example of FIG. 7 pertains to situations where the right ventricular contracts prior to the left ventricle, or, in other words, where $PR_{RV}$ is less than $PR_{LV}$ or $R_{RV}(t) < R_{LV}(t)$. Hence, a right ventricular channel 720 signal such as a QRS signal 724 can be used to terminate the AFF sensing window 735. Where the left ventricle contracts prior to the right ventricle, a QRS signal measured on the left ventricular channel may be used to terminate an AFF sensing window.

To help ensure that an atrial far-field signal includes contributions from left atrial activity, an electrode or electrodes positioned proximate to the left atrium may be used to acquire the far-field atrial signal 732 (see, e.g., the lead 106 of FIG. 1). For example, an electrode configuration for far-field atrial sensing can include one or more of the electrodes 123 and/or the electrode 124. Hence, the left ventricular channel 730 can acquire a far-field atrial signal 732 and a ventricular signal (e.g., QRS 732). Far-field atrial information can be analyzed for width, where a wider signal can indicate atrial asynchrony, issues with atrial conduction, etc. A far-field atrial signal can also reflect issues with left atrial pressures, mitral valve activity, etc., which often afflict heart failure patients.

An exemplary device includes an electrode configuration to sense near-field atrial activity, an electrode configuration to sense far-field atrial activity and an electrode configuration to sense ventricular activity. In this example, the same electrode configuration may be used to sense far-field atrial activity and ventricular activity. In general, however, the electrode configuration to sense far-field atrial activity is a unipolar configuration (e.g., include a can electrode) and the electrode configuration to sense ventricular activity is a combipolar configuration (e.g., bipolar).

An exemplary method includes acquiring a near-field atrial signal and a far-field atrial signal and assessing heart failure and CRT performance based at least in part on the signals. Such an assessment can be used to determine or select one or more parameter values for delivery of CRT. As mentioned, the method can include setting an atrial far-field sensing window, for example, based on an atrial event (e.g., detected using one or more right atrial electrodes) and a predetermined time interval or a ventricular event. In such a method, a ventricular sensing channel is optionally set to a sensing mode for a unipolar electrode configuration that relies on a can electrode where, for example, one or more lead-based electrodes may be electrically connected (e.g., one or more of the electrodes 123) to effectively increase sensing area.

An exemplary method includes acquiring information using a multiple electrodes on a left ventricular lead. Such information includes atrial activity information and optionally other information such as impedance information.

For bi-ventricular pacing, the main parameters are PV/AV and VV. Any of a variety of algorithms may be used to determine values for these parameters. Some algorithms that rely on IEGM information are described with respect to FIGS. 8 and 9. As mentioned, an implantable CRT may be configured to acquire IEGM information. Once acquired, IEGM information may be used by algorithms of the CRT device to optimize parameter values and/or used by algorithms of another computing device to optimize parameter values. As described in FIG. 6, HF and/or CRT performance assessments 682 may be based on one or more of the measurements 662 and/or one or more of the settings 672.

Figure 8:
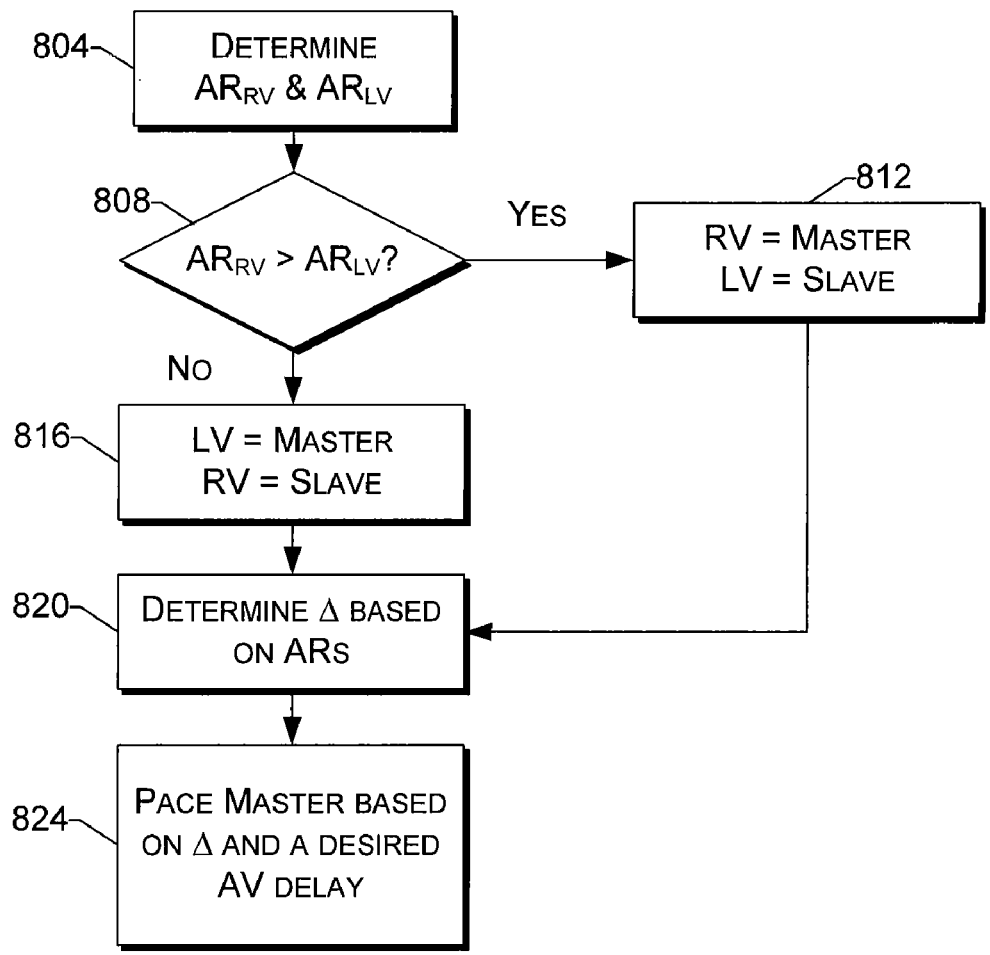
FIG. 8 is a block diagram of an exemplary method for ventricular pacing based on an $AR_{RV}$ time and an $AR_{LV}$ time.
Figure 9:
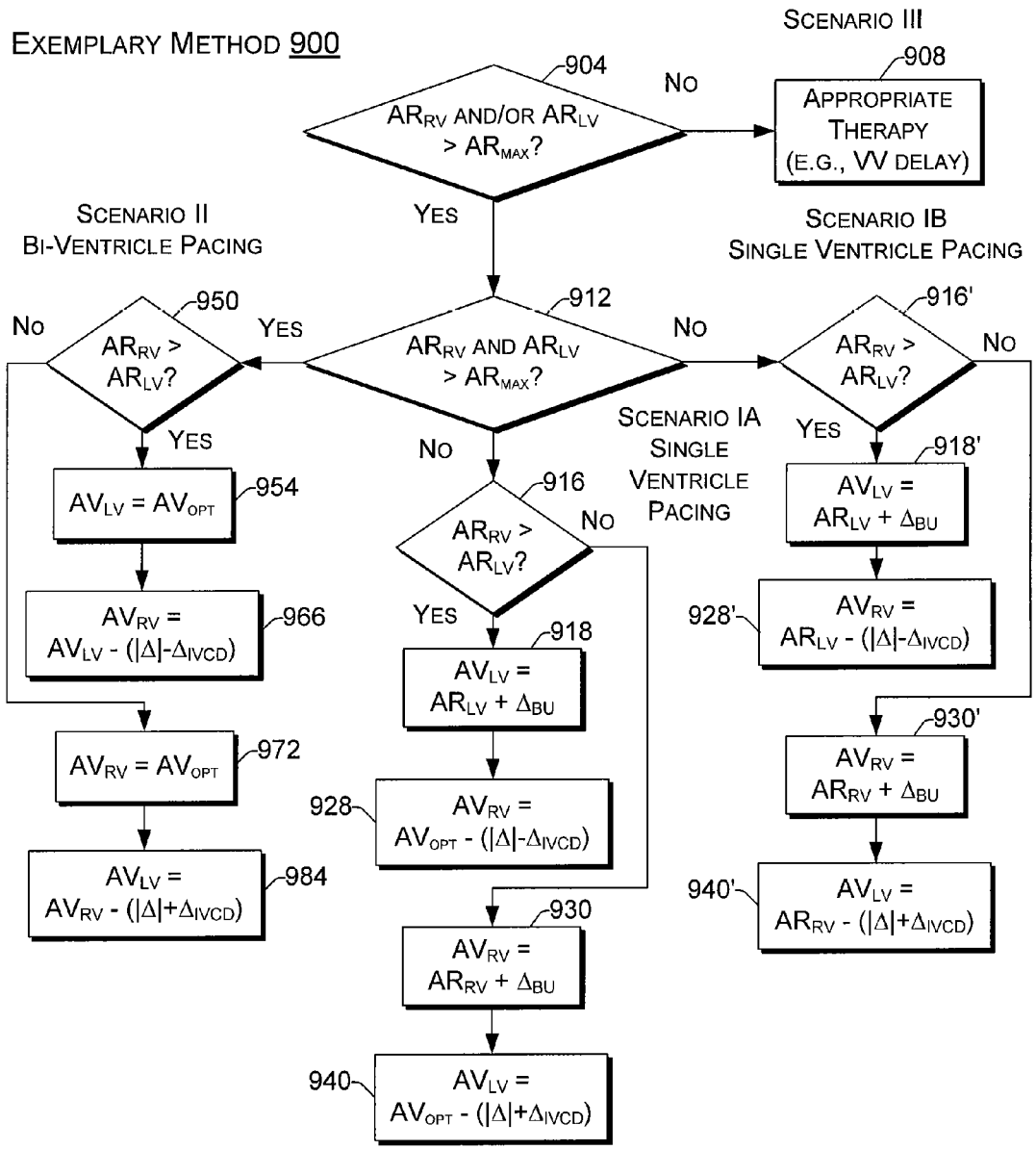
FIG. 9 is a block diagram of an exemplary method for ventricular pacing with scenarios for pacing a single ventricle and a scenario for pacing both ventricles.

FIGS. 8 and 9 show some algorithms that may be used to determine one or more CRT settings using measured IEGM information. For CRT, measurements and settings may include:

| | |
|---|---|
| PP, AA | Interval between successive atrial events (e.g., two beats) |
| PV | Delay between an atrial event and a paced ventricular event |
| $PV_{Opt}$ | Optimal PV delay |
| $PV_{RV}$ | PV delay for right ventricle |
| $PV_{LV}$ | PV delay for left ventricle |
| AV | Delay for a paced atrial event and a paced ventricular event |
| $AV_{Opt}$ | Optimal AV delay |
| $AV_{RV}$ | AV delay for right ventricle |
| $AV_{LV}$ | AV delay for left ventricle |
| Δ | Estimated interventricular delay (e.g., via IEGM), which may be calculated as $PR_{LV} - PR_{RV}$ or $AR_{LV} - AR_{RV}$ |
| IVCD-RL | Delay between an RV event and a consequent sensed LV event |
| IVCD-LR | Delay between an LV event and a consequent sensed RV event |
| $Δ_{IVCD}$ | IVCD-LR − IVCD-RL |
| ΔP, ΔA | Width of an atrial event |

FIG. 8 shows an exemplary method 800 for ventricular pacing. In a determination block 804, an implantable device determines an $AR_{RV}$ time and an $AR_{LV}$ time or equivalent times wherein one or both rely on detection of an intrinsic atrial event. A decision block 808 follows where a decision is made as to whether $AR_{RV}$ is greater than $AR_{LV}$. If $AR_{RV}$ exceeds $AR_{LV}$, then in a set block 812, the right ventricle is set to the master and the left ventricle is set to the slave. If $AR_{LV}$ exceeds $AR_{RV}$, then in a set block 816, the left ventricle is set to the master and the right ventricle is set to the slave. Both set blocks 812, 816 continue in a determination block 820 which determines a Δ value based on the $AR_{RV}$ and $AR_{LV}$ times. A pace master block 824 follows where the master ventricle is paced based on the Δ and a desired AV delay. The desired AV delay may be determined, for example, based on echocardiography or other study. The AV delay is optionally determined by an implantable device based on sensed information. Various techniques may use sensed information such as width of a P wave (ΔP) or width of an A wave (ΔA) to determine one or more settings.

Thus, as described with respect to FIG. 8, such an exemplary method includes determining an atrial to ventricular activation time for a right ventricle, determining an atrial to ventricular activation time for a left ventricle, and determining a pacing sequence that paces the right ventricle prior to activation of the left ventricle if the time for the right ventricle exceeds the time for the left ventricle or that paces the left ventricle prior to activation of the right ventricle if the time for the left ventricle exceeds the time for the right ventricle where pacing of the prior activated ventricle occurs based at least in part on a difference between the time for the right ventricle and the time for the left ventricle and a desired atrio-ventricular delay. In some instances, an interventricular delay may be used instead of, or in addition, to one or more atrial to ventricular activation times.

FIG. 9 shows an exemplary method 900 that can use an interventricular conduction delay differential ($\Delta_{IVCD}$) to determine an atrio-ventricular parameter value. While the method 900 pertains to atrial pacing, such a method may omit atrial pacing (e.g., rely on an intrinsic atrial activity, etc.) and/or include atrial pacing and intrinsic atrial activity, etc. (e.g., PR, AR, AV, and/or PV). The exemplary method 900 includes Scenarios IA, IB, II and III.

In a decision block 904 a decision is made as to whether $AR_{RV}$ and/or $AR_{LV}$ have exceeded a predetermined $AR_{max}$ value. If neither value exceeds $AR_{max}$, then Scenario III follows, which may disable ventricular pacing or take other appropriate therapy per block 908. Other appropriate therapy optionally includes therapy that achieves a desirable VV delay by any of a variety of techniques. If however one or both values exceed $AR_{max}$, then the method 900 continues in another decision block 912. The decision block 912 decides whether $AR_{RV}$ and $AR_{LV}$ have exceeded $AR_{max}$. If both values do not exceed $AR_{max}$, then single ventricular pacing occurs, for example, per Scenario IA or Scenario IB. If both values exceed $AR_{max}$, then bi-ventricular pacing occurs, for example, Scenario II.

Scenario IA commences with a decision block 916 that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IA, the method 900 continues in a back-up pacing block 918 where $AV_{LV}$ is set to $AR_{LV}$ plus some back-up time (e.g., $\Delta_{BU}$). The block 918, while optional, acts to ensure that pacing will occur in the left ventricle if no activity occurs within some given interval. The method 900 then continues in a set block 828 where the parameter $\Delta_{IVCD}$ is used as a correction factor to set the $AV_{RV}$ delay to $AV_{optimal}-(|\Delta|-\Delta_{IVCD})$.

For left ventricular pacing per the Scenario IA, the method 900 continues in a back-up pacing block 930 where $AV_{RV}$ is set to $AR_{RV}$ plus some back-up time (e.g., $\Delta_{BU}$). The block 930, while optional, acts to ensure that pacing will occur in the left ventricle if no activity occurs within some given interval. The method 900 then continues in a set block 940 where the parameter $\Delta_{IVCD}$ is used as a correction factor to set the $AV_{LV}$ delay to $AV_{optimal}-(|\Delta|+\Delta_{IVCD})$.

Scenario IB commences with a decision block 916' that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IB, the method 900 continues in a back-up pacing block 918' where $AV_{LV}$ is set to $AR_{LV}$ plus some back-up time (e.g., $\Delta_{BU}$). The block 918', while optional, acts to ensure that pacing will occur in the left ventricle if no activity occurs within some given interval. The method 900 then continues in a set block 928' where the parameter $\Delta_{IVCD}$ is used as a correction factor to set the $AV_{RV}$ delay to $AR_{LV}-(|\Delta|-\Delta_{IVCD})$. Hence, in this example, a pre-determined $AV_{optimal}$ is not necessary.

For left ventricular pacing per the Scenario IB, the method 900 continues in a back-up pacing block 930' where $AV_{RV}$ is set to $AR_{RV}$ plus some back-up time (e.g., $\Delta_{BU}$). The block 930', while optional, acts to ensure that pacing will occur in the left ventricle if no activity occurs within some given interval. The method 900 then continues in a set block 940' where the parameter $\Delta_{IVCD}$ is used as a correction factor to set the $AV_{LV}$ delay to $AR_{RV}-(|\Delta|+\Delta_{IVCD})$. Again, in this example, a pre-determined $AV_{optimal}$ is not necessary.

Referring again to the decision block 912, if this block decides that bi-ventricular pacing is appropriate, for example, Scenario II, then the method 900 continues in a decision block 950, which that decides if $AR_{RV}$ is greater than $AR_{LV}$. If $AR_{RV}$ exceeds $AR_{LV}$, then bi-ventricular pacing occurs wherein the right ventricle is the master (e.g., paced prior to the left ventricle or sometimes referred to as left ventricle slave). If $AR_{RV}$ does not exceed $AR_{LV}$, then bi-ventricular pacing occurs wherein the left ventricle is the master (e.g., paced prior to the right ventricle or sometimes referred to as right ventricle slave).

For right ventricular master pacing, the method 900 continues in a set block 954 which sets $AV_{LV}$ to $AV_{optimal}$. The method 900 then uses $\Delta_{IVCD}$ as a correction factor in a set block 966, which sets $AV_{RV}$ delay to $AV_{LV}-(|\Delta|-\Delta_{IVCD})$.

For left ventricular master pacing, the method 900 continues in a set block 972 which sets $AV_{RV}$ to $AV_{optimal}$. The method 900 then uses $\Delta_{IVCD}$ as a correction factor in a set block 884, which sets $AV_{LV}$ delay to $AV_{RV}-(|\Delta|+\Delta_{IVCD})$.

A comparison between $\Delta$ as measured using IEGM information and $\Delta_{programmed}$ or $\Delta_{optimal}$ can indicate a difference between a current cardiac therapy or state and a potentially better cardiac therapy or state. For example, consider the following equation:

$$\alpha = \Delta_{optimal}/\Delta$$

where $\alpha$ is an optimization parameter. Various echocardiogram studies indicate that the parameter $\alpha$ is typically about 0.5. The use of such an optimization parameter is optional. The parameter $\alpha$ may be used as follows:

$$AV_{RV}=AV_{optimal}-\alpha|\Delta| \text{ or } PV_{RV}=PV_{optimal}-\alpha|\Delta|$$

$$AV_{LV}=AV_{optimal}-\alpha(|\Delta|+\Delta_{IVCD}) \text{ or}$$

$$PV_{LV}=PV_{optimal}-\alpha(|\Delta|+\Delta_{IVCD})$$

If a parameter such as the aforementioned $\alpha$ parameter is available, then such a parameter is optionally used to further adjust and/or set one or more delays, as appropriate.

Various exemplary methods, devices, systems, etc., may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equation may be used in such a situation:

$$AV_{LV}=AR_{RV}-|\Delta| \text{ or } PV_{LV}=PR_{RV}-|\Delta|$$

This equation is similar to the equation used in blocks 928' and 940' of Scenario IB of FIG. 9. With respect to backup pulses, a backup pulse (e.g., for purposes of safety, etc.) may be set according to the following equation:

$$AV_{RV}=AR_{RV}+|\gamma| \text{ or } PV_{RV}=PR_{RV}+|\gamma|$$

Of course, administration of a backup pulse may occur upon one or more conditions, for example, failure to detect activity in the particular ventricle within a given period of time. In the foregoing equation, the parameter γ is a short time delay, for example, of approximately 5 ms to approximately 10 ms. This equation is similar to the equation used in blocks 918' and 930' of Scenario IB of FIG. 9.

In many instances, heart condition will affect $AR_{RV}$ and $AR_{LV}$, and IVCD (e.g., IVCD-RL and/or IVCD-LR), which, in turn, may affect an existing optimal VV delay setting. Various exemplary methods, devices, systems, etc., include triggering of an algorithm to update an existing optimal VV delay according to a predetermined time or event period or activity sensors for exercise, resting, etc. An exemplary device may include a learning method that learns based on differences in conduction times (e.g., $AR_{RV}$ and $AR_{LV}$, IVCD, etc.) such that parameters associated with different heart demands can be stored. The exemplary learning method may then extract such learned or other parameters to set an optimal VV delay. As discussed further below, the neural model 1400 of FIG. 14 may be used in a learning scheme for setting parameters and/or for assessing HF and/or CRT performance.

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

Figure 10:
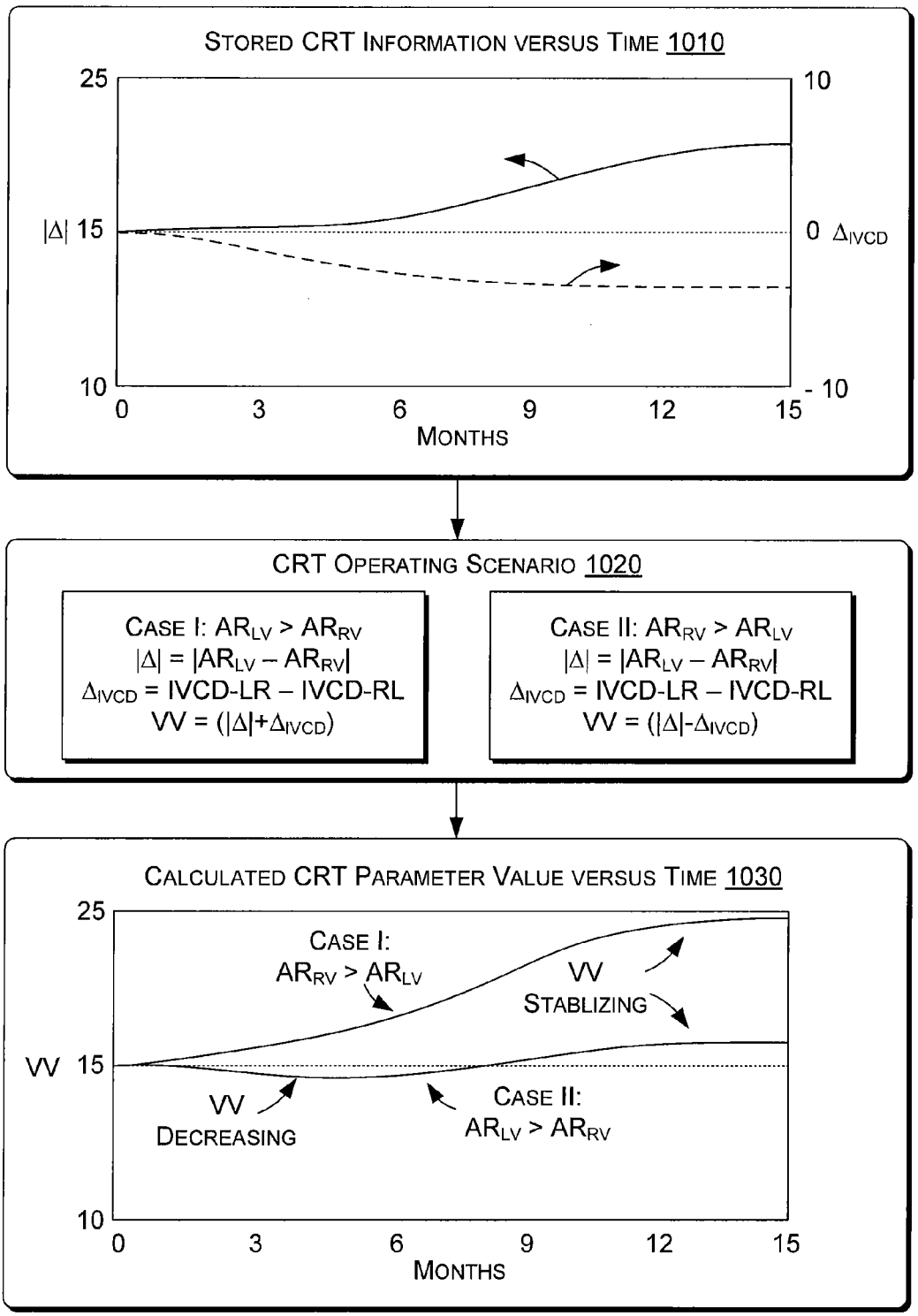
FIG. 10 is a block diagram of an exemplary method for analyzing one or more CRT parameter values over time.

FIG. 10 shows an exemplary method 1000 that relies on historical information to assess HF and/or CRT performance. The method 1000 includes storing CRT information versus time per the plot 1010. The plot 1010 includes values for the parameters Δ and $\Delta_{IVCD}$ over a period of months. At an initial time (e.g., 0 months), the parameter Δ was about 15 ms and the parameter $\Delta_{IVCD}$ was about 0 ms. However, over a period of months, the absolute value of the parameter Δ increased and the parameter $\Delta_{IVCD}$ decreased. A decreasing $\Delta_{IVCD}$ value means that the right to left interventricular conduction delay is increasing and/or that the left to right interventricular conduction delay is decreasing.

As explained with respect to the method 900 of FIG. 9, the interventricular delay may depend on Δ and $\Delta_{IVCD}$. The particular relationship between interventricular delay and Δ and $\Delta_{IVCD}$ depends on intrinsic atrio-ventricular conduction for the right ventricle and the left ventricle. More specifically, the method 1000 depends on the CRT operating scenario 1020. In the example of FIG. 10, the scenario corresponds to Scenario II of the method 900, which has two cases: Case I $AR_{LV} > AR_{RV}$ and Case II $AR_{RV} > AR_{LV}$. As $\Delta_{IVCD}$ is defined as IVCD-LR−IVCD-RL, the sign for $\Delta_{IVCD}$ differs for Case I and Case II. In turn, the stored information affects the interventricular delay (VV) differently for Case I and Case II. Calculated CRT parameter values versus time are shown in a plot 1030. As indicated, for Case I, the VV delay increases by about 10 ms while for Case II, the VV delay remains relatively constant. For Case I and Case II, the change over time diminishes around 12 months, which may indicate that the patient's condition is stabilizing.

For the method 1000, to assess patient condition (e.g., HF) and/or CRT performance, knowledge of measured values and algorithms for determining CRT parameter values are helpful. In particular, an assessment of CRT performance based on VV benefits from knowing whether the patient was paced according to Case I or Case II.

Figure 11:
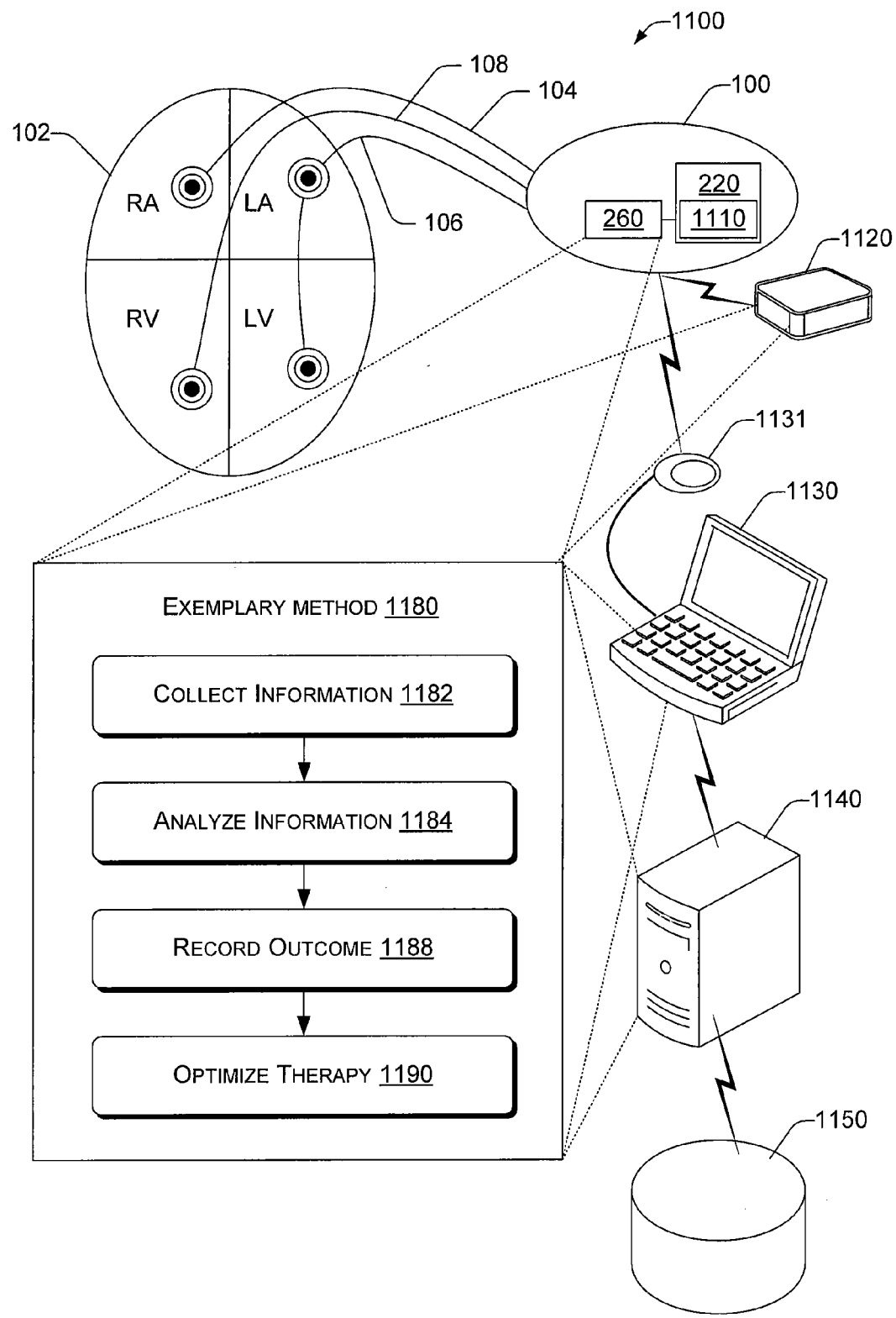
FIG. 11 is a block diagram of an exemplary system for acquiring information, analyzing information and monitoring HF and/or CRT performance.

FIG. 11 shows an exemplary system 1100 for implementing an exemplary method 1180, noting that the system 1100 may implement various methods described herein. The system 1100 that includes the exemplary implantable device 100 of FIGS. 1 and 2, with processor 220 including one or more modules 1110, for example, that may be loaded via memory 260. A series of leads 104, 106 and 108 provide for delivery of stimulation energy and/or sensing of cardiac activity, etc., associated with the heart 102. Stylized bullets indicate approximate positions or functionality associated with each of the leads 104, 106 and 108. Other arrangements are possible as well as use of other types of sensors, electrodes, etc.

The system 1100 includes a device programmer 1130 having a wand unit 1131 for communicating with the implantable device 100. The programmer 1130 may further include communication circuitry for communication with another computing device 1140, which may be a server. The computing device 1140 may be configured to access one or more data stores 1150, for example, such as a database of information germane to a patient, an implantable device, therapies, etc.

The programmer 1130 and/or the computing device 1140 may include various information and modules (e.g., processor-executable instructions) for performing one or more steps of the method 1180. The programmer 1130 optionally includes features of the commercially available 3510 programmer and/or the MERLIN™ programmer marketed by St. Jude Medical, Sylmar, Calif. The MERLIN™ programmer includes a processor, ECC (error-correction code) memory, a touch screen, an internal printer, I/O interfaces such as a USB that allows a device to connect to the internal printer and attachment of external peripherals such as flash drives, Ethernet, modem and WiFi network interfaces connected through a PCMCIA/CardBus interface, and interfaces to ECG and RF (radio frequency) telemetry equipment. The programmer 1030 may be capable of displaying the GUI 531 of FIG. 5, for example, to enable the method 1080.

The wand unit 1131 optionally includes features of commercially available wands. As shown, the wand unit 1131 attaches to the programmer 1130, which enables clinicians to conduct implantation testing and performance threshold testing, as well as programming and interrogation of pacemakers, implantable cardioverter defibrillators (ICDs), emerging indications devices, etc.

During implant, a system such as a pacing system analyzer (PSA) may be used to acquire information, for example, via one or more leads. A commercially available device marketed as WANDA™ (St. Jude Medical, Sylmar, Calif.) may be used in conjunction with a programmer such as the MERLIN™ programmer or other computing device (e.g., a device that includes a processor to operate according to firmware, software, etc.). Various exemplary techniques described herein may be implemented during implantation and/or after implantation of a device for delivery of electrical stimulation (e.g., leads and/or pulse generator) and the types of equipment for acquiring and/or analyzing information may be selected accordingly.

The wand unit 1131 and the programmer 1130 allow for display of atrial and ventricular electrograms simultaneously during a testing procedure. Relevant test measurements, along with customizable implant data, can be displayed, stored, and/or printed in a comprehensive summary report for the patient's medical records and physician review and/or for other purposes.

In the example of FIG. 11, the data store 1150 may include information such as measures, values, scores, etc. Such information may be used by a model, in making a comparison, in making a decision, in adjusting a therapy, etc. Such information may be updated periodically, for example, as the device 100 (or other device(s)) acquires new patient information. The system 1000 is an example as other equipment, instructions, etc., may be used or substituted for features shown in FIG. 11.

While FIG. 11 shows method 1180, the system 1100 or components thereof may be used to implement other methods described herein. The method 1180 includes a collection block 1182 for collecting information, an analysis block 1084 for analyzing information, a recordation block 1188 for recording outcomes and an optimization block 1190 for optimizing patient therapy. Collected information can include one or more measures, pacing parameters, historical interval values, etc. Part or all of the method 1180 may be performed using a device other than the implantable device 100. For example, the housecall device 1120, the device programmer 1130 and/or the computing device 1140 may perform one or more steps of the method 1180 and/or provide information. The dashed lines indicate that the instruction blocks of the method 1180 may be loaded into memory of the implantable device 100, the housecall device 1120, the device programmer 1130 and/or the computing device 1140. Further, various methods and/or information may be stored in the data store 1150 and accessed as desired.

In the system 1100 of FIG. 11, a single implantable device 100 is shown, however, such a system interact with include multiple implantable devices. For example, the device programmer 1130 may be associated with a clinician at a hospital that cares for many CRT patients. The clinician may store information in the data store 1150 and rely on aggregated information when planning or adjusting treatment for one or more patients. In particular, outcome measures for each patient may be recorded and used to more effectively treat patients.

Figure 12:
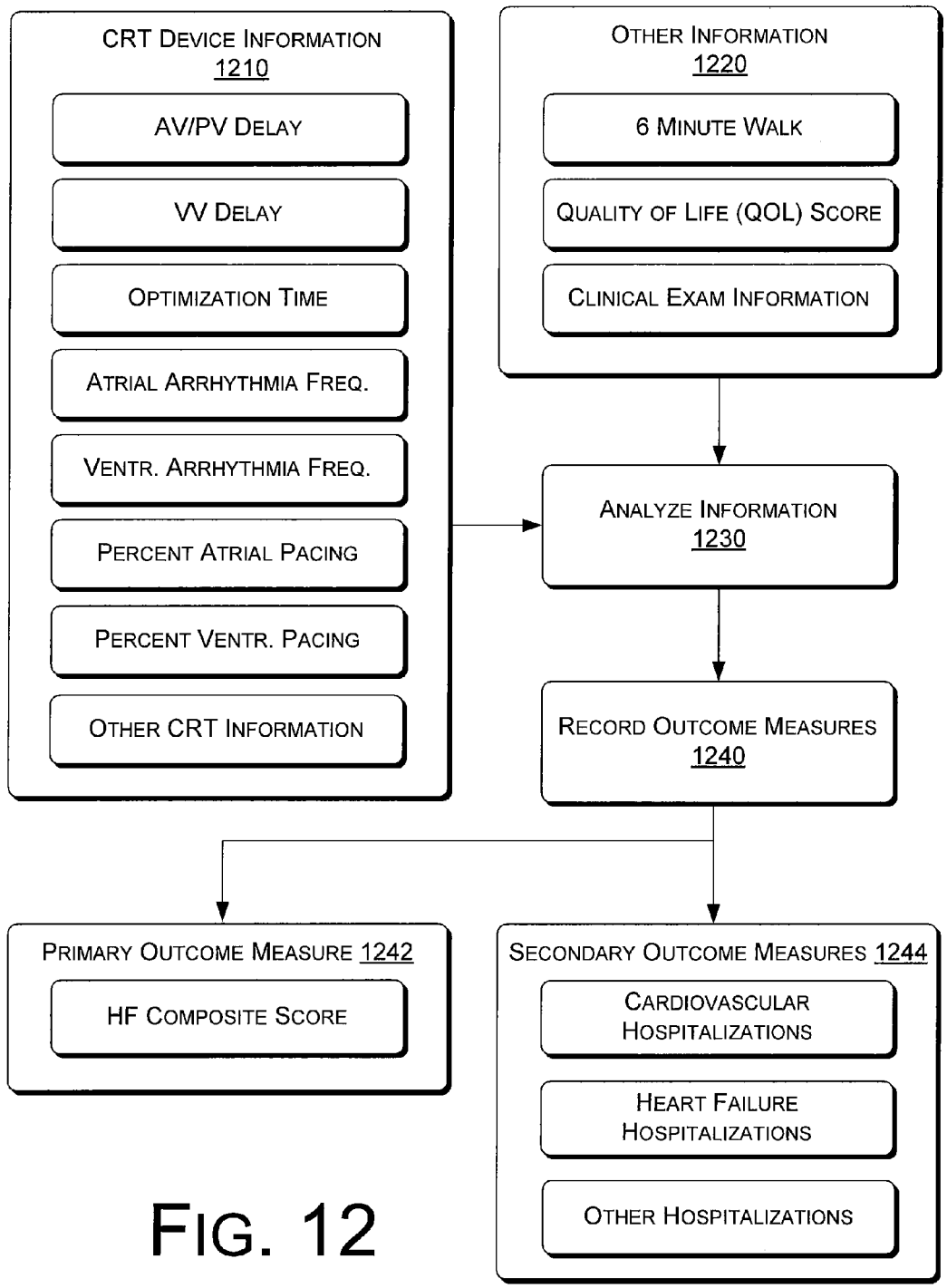
FIG. 12 is a block diagram of an exemplary method for analyzing information and recording outcomes.

FIG. 12 shows an exemplary method 1200 that for recording patient outcome measures with respect to CRT. The method 1200 can acquire CRT device information 1210 and other information 1220, analyze the acquired information 1230 and record outcome measures 1240 such as a primary outcome measure 1242 and secondary outcome measures 1244. In general, a primary outcome is an outcome that provides the primary measure of the effectiveness (or lack of effectiveness) of an intervention, which in this instance pertains to CRT, including sub-groups of CRT; whereas, secondary outcomes are typically events, variables, or experiences that are of secondary interest. The method 1200 may be implemented using the system 1100 and optionally record outcome measures related to clinical trials.

In the example of FIG. 12, the CRT device information 1210 includes any of a variety of information pertaining to CRT. For example, CRT device information 1210 can include AV/PV delay, VV delay, optimization time (time required for an algorithm to optimize one or more CRT parameter values), atrial arrhythmia frequency, ventricular arrhythmia frequency, percent atrial pacing, percent ventricular pacing (including percent bi-ventricular pacing, see, e.g., FIG. 9) and other CRT related information.

In the method 1200, other information 1220 may be provided by a clinician during a patient examination or it may be information provided by a patient in responding to a questionnaire, a home blood pressure monitor, home exercise equipment, etc. In the example of FIG. 12, the information 1220 includes data from a six minute walk test, a quality of life score (QOL) and information from a clinical examination. In general, the information 1220 does not come from a CRT device, however, it may come from a housecall device or other source. Thus, the method 1200 is capable of combining information acquired from a CRT device 1210 and information acquired from one or more other sources 1220.

With respect to analysis of information 1230, CRT device information 1210 and/or other information 1220 may be selected for particular analyses. Filters may be used to select information according to one or more criteria. Such criteria may correspond to periods of time (e.g., a month, a week, etc.), patient activity (e.g., rest or active), pacing therapy (e.g., atrial pacing, ventricular pacing, bi-ventricular pacing), arrhythmias, CRT parameter value ranges (e.g., VV delay less than a limit or between two limits), etc.

With respect to recording outcome measures 1240, a commonly used primary outcome measure 1242 is an HF composite score. Such a score may be calculated in any of a variety of manners. HF composite scores may rely assessment of left ventricular function (e.g., how the left chamber of the heart is pumping), use of medications (e.g., use of ACE inhibitors to treat decreased heart function, heart attacks or heart failure), patient behavior (e.g., smoking cessation), etc. Standard HF assessment scores include the New York Heart Association classifications (Class I to Class IV) and the Boston Criteria for diagnosing HF. The Boston Criteria assign points for conditions such as rest dyspnea, orthopnea, paroxysmal nocturnal dyspnea, dyspnea while walking on level area, dyspnea while climbing, heart rate abnormality, jugular venous elevation results, lung crackles, wheezing, third heart sound, alveolar pulmonary edema, interstitial pulmonary edema, bilateral pleural effusion, particular cardiothoracic ratio values and upper zone flow redistribution.

With respect to secondary outcome measures 1244, these may include hospitalization due to cardiovascular condition, hospitalization due to heart failure, other hospitalizations and/or other measures of secondary interest.

Figure 13:
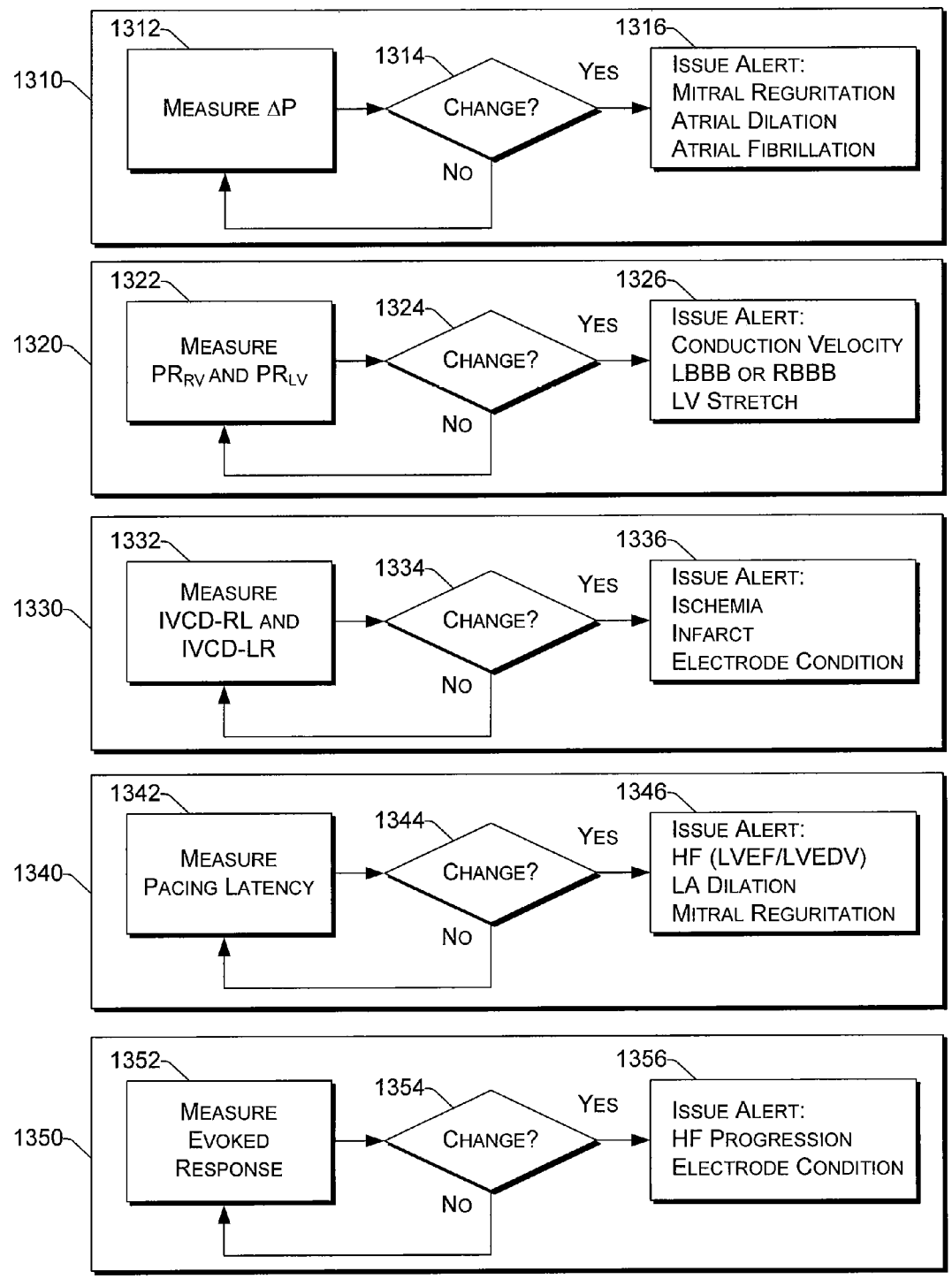
FIG. 13 is a block diagram of a series of exemplary methods for deciding whether to further assess patient condition.

FIG. 13 shows a series of exemplary methods 1310, 1320, 1330, 1340 and 1350 that indicate how a measure acquired by an implantable CRT device may be used to issue an alert. In the examples of FIG. 13, each of the methods includes a decision block that decides whether a change occurred. Various alternatives exist for such decisions, for example, a limit or limits may be used to decide if a measure should trigger an alert.

The method 1310 includes a measurement block 1312 for measuring P wave or A wave width ($\Delta P$). The measure $\Delta P$ can be an indicator of atrial conduction heterogeneity and, more generally, interatrial conduction, noting that the technique 700 can be used to acquire information indicative of conduction heterogeneity. A decision block 1314 decides if a change occurred for $\Delta P$. If a change occurred, for example, according to one or more criteria, then an alert block 1316 issues an alert to check one or more conditions such as mitral regurgitation, atrial dilation and atrial fibrillation. Intrinsic P wave width and paced A wave width may be used separately or together to predict atrial remodeling, for example, as related to LA dilation. Other information such as pacing latency in atria may also be used in conjunction with $\Delta P$.

The method 1320 includes a measurement block 1322 for measuring $PR_{RV}$ and $PR_{LV}$ (or $AR_{RV}$ and $AR_{LV}$). These measures can be an indicator of AV nodal condition and bundle branch condition. Further, as AV conduction is affected by autonomic tone, a change in tone toward sympathetic or toward parasympathetic may result in a change in one or more of these measures. A decision block 1324 decides if a change in any of these measures has occurred. If a change occurred, for example, according to one or more criteria, then an alert block 1326 issues an alert to check one or more conditions such as conduction velocity, LBBB, RBBB and LV stretch.

The method 1330 includes a measurement block 1332 for measuring IVCD-RL and IVCD-LR. These measures can be an indicator of conduction in the ventricular myocardium. A decision block 1334 decides if a change in any of these measures has occurred. If a change occurred, for example, according to one or more criteria, then an alert block 1336 issues an alert to check one or more conditions such as ischemia, infarct, and electrode condition.

The method 1340 includes a measurement block 1342 for measuring pacing latency at one or more locations. This measure can be an indicator of conduction in the myocardium (e.g., atrial or ventricular). A decision block 1344 decides if a change in this measure has occurred. If a change occurred, for example, according to one or more criteria, then an alert block 1346 issues an alert to check one or more conditions such as HF (e.g., LVEF, LVEDV), LA dilation and mitral regurgitation.

The method 1350 includes a measurement block 1352 for measuring one or more evoked response characteristics at one or more locations. This measure can be an indicator of conduction in the myocardium (e.g., atrial or ventricular), refractoriness, etc. A decision block 1354 decides if a change in this measure has occurred. If a change occurred, for example, according to one or more criteria, then an alert block 1356 issues an alert to check one or more conditions such as HF progression and electrode condition.

The following table indicates some trends that may be used to assess patient condition and possible outcomes:

| Correction Term ($\Delta_{IVCD}$) | Conduction Delays | P wave width ($\Delta P$) | Possible Clinical Outcomes |
|---|---|---|---|
| ↑ | ↑ | ↑ | MR, LV/LA dilation |
| ↓ | ↓ | ↓ | Reverse remodeling |

For example, if pacing latency and conduction delays increase and ER amplitude decreases, this can be a specific indicator for HF progression. A scoring system for quantifying patient condition or CRT performance can be defined based on changes measured so that the degree of HF exacerbation can be more readily accessed.

As mentioned, an optimization algorithm such as the QUICKOPT™ algorithm calls for a variety of measures. Such measures include intra-atrial conduction delay (A sense and A pace tests), atrio-ventricular conduction delay (V sense test), interventricular conduction delay (RV pace and LV pace test) and other measures that may reflect abnormalities in conduction delay (e.g., pacing latency). These measures may be used in any of a variety of combinations as indicators for HF status. Intra-atrial conduction delay (A sense and A pace tests) may relate to severity of MR and dilation of LA, AF. Atrio-ventricle conduction delay (V sense test) and PR to RV and LV and the difference of between such measures can indicate changes in both conduction velocity and stretch of the LV. Interventricular conduction delays (RV pace and LV pace tests) can be predictors for combined effect of conduction velocity changes and LV dimension, pacing latency. The correction term ($\Delta_{IVCD}$, difference in LV pace and RV pace tests) can indicate directional conduction and include effects due to pacing latency. This term can also indicate the severity of ischemia, infarct regions or if the site of RV and LV leads are in or near infarcts. Pacing latency (time interval from delivery of a stimulus to an evoked response signal) can be used to monitor atrial and ventricular disease status, which includes HF status, AF and renal dysfunction. For HF status, pacing latency in the LV and/or the RV can be a surrogate for left ventricular ejection fraction (LVEF) and/or left ventricular end-diastolic volume (LVEDV). Pacing latency in the LA can be used to predict and/or monitor LA dilation or the degree of mitral regurgitation (MR), etc. A combination of atrial and ventricular pacing latency can increase specificity for assessments. Again, the QUICKOPT™ algorithm can call for "A pace", "RV Pace" and "LV pace" tests to provide measures as well as providing measures of pacing latency. In turn, these QUICKOPT™ tests can be used to monitor HF exacerbation and CRT performance (reverse remodeling, etc.).

Figure 14:
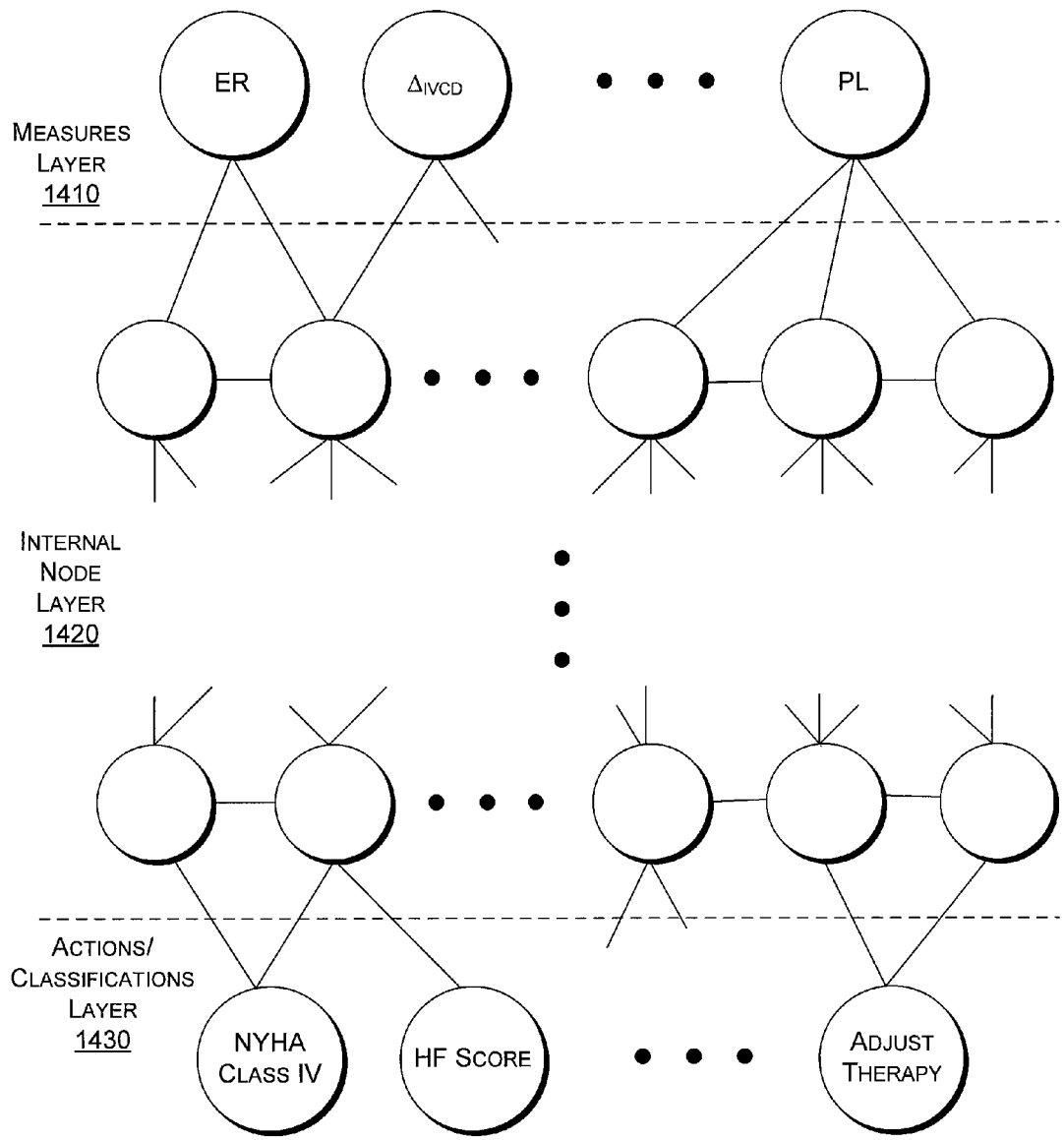
FIG. 14 is a diagram of an exemplary neural model for establishing relationships between measures and actions or classifications related to cardiac condition and/or CRT performance.

FIG. 14 shows an exemplary neural model 1400 that includes a measures layer 1410, an internal node layer 1420 and an actions/classifications layer 1430. The model 1400 may rely on any of a variety of probabilistic techniques to recommend actions for CRT or to classify patient condition. For example, the model 1400 may be neural network that uses non-linear statistical data modeling to model complex relationships between inputs and outputs or to find patterns in data. The model 1400 may be an adaptive or learning system that changes its structure based on external or internal information that flows through the network.

The measures layer 1410 may include one or more measures such as one or more of the measurements 662 of FIG. 6. The actions/classifications layer 1430 may include any of a variety of actions related to CRT and/or HF. In general, a model is trained using training data and then provided data to determine recommended courses of action or classifications. While a single model is shown in FIG. 14, an exemplary method may rely on more than one model, which may be independent of each other or include some dependency.

Various exemplary methods described herein can be implemented on one or more devices. In one embodiment, the steps 320, 330, 340 and 350 and/or 360 are implemented using a CRT device such as the device 100 of FIGS. 1 and 2. In another embodiment, the steps 320, 330, 340 and 350 and/or 360 are implemented using a CRT device such as the device 100 of FIGS. 1 and 2 and another device, which may be a device programmer (e.g., device 530 of FIG. 5) or a housecall device (e.g., device 510 of FIG. 5).

An exemplary system includes an implantable CRT device and a housecall device that operate in a patient environment where the CRT device performs tests to acquire measures and where the housecall device downloads measures daily or periodically. Such information can then be analyzed and used to determine one or more optimal parameter values for CRT. In this example, the housecall device can program the CRT device to deliver CRT using the one or more optimal parameters. In various embodiments, information from a CRT device can be used in conjunction with clinical test information such as weigh watch, blood pressure, etc. As shown in the series of method 1310-1350 of FIG. 13, warning signals or alerts may be issued for possible clinical risks. For example, a housecall device 510 optionally includes circuitry for issuing alerts to a clinician or other service provider. Such alerts may be issued via a network (e.g., the Internet, a telephone network, etc.).

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method comprising:
    delivering a cardiac resynchronization therapy that comprises an atrio-ventricular delay parameter and an interventricular delay parameter;
    measuring an intrinsic atrio-ventricular conduction delay;
    measuring an intrinsic interventricular conduction delay;
    assessing heart failure status based at least in part on the measured atrio-ventricular conduction delay and the measured interventricular conduction delay; and
    adjusting at least one of the atrio-ventricular delay parameter value and the interventricular delay parameter value based at least in part on the measured atrio-ventricular conduction delay and the measured interventricular conduction delay.

2. The method of claim 1 further comprising assessing cardiac resynchronization therapy performance based at least in part on the measured atrio-ventricular conduction delay and the measured interventricular conduction delay.

3. The method of claim 1 further comprising measuring an intrinsic P wave width and using the measured P wave width in the assessing heart failure.

4. The method of claim 1 further comprising measuring an intrinsic P wave width and using the measured P wave width in the determining at least one of an atrio-ventricular delay parameter value and an interventricular delay parameter value.

5. The method of claim 1 further comprising measuring a paced A wave width and using the measured A wave width in the assessing heart failure.

6. The method of claim 1 further comprising measuring a paced A wave width and using the measured A wave width in the determining at least one of an atrio-ventricular delay parameter value and an interventricular delay parameter value.

7. The method of claim 1 further comprising measuring pacing latency and using the measured pacing latency in the assessing heart failure.

8. The method of claim 1 further comprising measuring one or more evoked response characteristics and using the one or more measured characteristics in the assessing heart failure.

9. The method of claim 1 further comprising measuring impedance and using the measured impedance in the assessing heart failure.

10. The method of claim 1 further comprising transmitting information from the cardiac resynchronization therapy device to another device.

11. The method of claim 10 wherein the other device comprises a computing device configured to establish a communication link to the cardiac resynchronization therapy device and to operate in a patient environment.

12. A method comprising:
    delivering a cardiac resynchronization therapy that comprises an atrio-ventricular delay parameter and an interventricular delay parameter;
    measuring an atrio-ventricular conduction delay;
    measuring an interventricular conduction delay;
    assessing cardiac resynchronization therapy performance based at least in part on the measured atrio-ventricular conduction delay and the measured interventricular conduction delay; and
    determining at least one of an atrio-ventricular delay parameter value and an interventricular delay parameter value based at least in part on the measured atrio-ventricular conduction delay and the measured interventricular conduction delay.

13. The method of claim 12 further comprising measuring pacing latency and using the measured pacing latency in the assessing cardiac resynchronization therapy performance.

14. The method of claim 12 further comprising measuring one or more evoked response characteristics and using the one or more measured characteristics in the assessing cardiac resynchronization therapy performance.

15. The method of claim 12 further comprising measuring impedance and using the measured impedance in the assessing cardiac resynchronization therapy performance.

16. An implantable medical device comprising:
    stimulation circuitry that delivers cardiac resynchronization therapy that comprises an atrio-ventricular delay parameter and an interventricular delay parameter;
    sensing circuitry that measures an intrinsic atrio-ventricular conduction delay and an intrinsic interventricular conduction delay;
    assessment circuitry that assesses heart failure status based at least in part on the measured atrio-ventricular conduction delay and the measured interventricular conduction delay; and
    wherein the stimulation circuitry adjusts at least one of the atrio-ventricular delay parameter value and the interventricular delay parameter value based at least in part on the measured atrio-ventricular conduction delay and the measured interventricular conduction delay.

17. The implantable medical device of claim 16 wherein the sensing circuitry measures pacing latency; and wherein the assessment circuitry uses the measured pacing latency to assess heart failure status.

18. The implantable medical device of claim 16 wherein the sensing circuitry measures one or more evoked response characteristics; and wherein the assessment circuitry uses the one or more measured characteristics to assess heart failure status.

19. The implantable medical device of claim 16 wherein the sensing circuitry measures impedance; and wherein the assessment circuitry uses the measured impedance to assess heart failure status.

20. The implantable medical device of claim 16 and further comprising telemetry circuitry to transmit information from the implantable medical device to another device.

* * * * *